United States Patent
Lee et al.

(10) Patent No.: US 12,283,378 B2
(45) Date of Patent: Apr. 22, 2025

(54) PROVIDING HEALTHCARE VIA AUTONOMOUS, SELF-LEARNING, AND SELF-EVOLUTIONARY PROCESSES

(71) Applicant: Planned Systems International, Inc., Arlington, VA (US)

(72) Inventors: June Lee, North Bethesda, MD (US); Gary L. Shaffer, Annapolis, MD (US); Thomas J Berti, Lusby, MD (US); Yan Li, Bethesda, MD (US)

(73) Assignees: Planned Systems International, Inc., Arlington, MD (US); National Society of Medical Scientists Inc., Bethesda, MD (US)

( * ) Notice: Subject to any disclaimer, the term of this patent is extended or adjusted under 35 U.S.C. 154(b) by 233 days.

(21) Appl. No.: 17/836,264

(22) Filed: Jun. 9, 2022

(65) Prior Publication Data
US 2023/0402178 A1 Dec. 14, 2023

(51) Int. Cl.
*G16H 50/20* (2018.01)
*A61B 34/32* (2016.01)
*G16H 20/00* (2018.01)
*G16H 20/10* (2018.01)
*G16H 20/40* (2018.01)
*G16H 40/60* (2018.01)

(52) U.S. Cl.
CPC ............ *G16H 50/20* (2018.01); *A61B 34/32* (2016.02); *G16H 20/00* (2018.01); *G16H 20/10* (2018.01); *G16H 20/40* (2018.01); *G16H 40/60* (2018.01)

(58) Field of Classification Search
CPC ........ G16H 20/10; G16H 20/40; G16H 40/60; G16H 50/20; G16H 20/00; G16H 50/70; G16H 40/67; A61B 34/32
See application file for complete search history.

(56) References Cited

U.S. PATENT DOCUMENTS

| | | | |
|---|---|---|---|
| 11,478,314 B1 * | 10/2022 | Roh | G16H 40/63 |
| 2011/0130636 A1 | 6/2011 | Daniel et al. | |
| 2016/0244163 A1 | 8/2016 | Peeters et al. | |
| 2017/0092109 A1 | 3/2017 | Trundle et al. | |
| 2018/0182475 A1 * | 6/2018 | Cossler | G16H 50/50 |
| 2019/0008598 A1 * | 1/2019 | Frimer | G16H 30/40 |
| 2019/0262084 A1 * | 8/2019 | Roh | G16H 20/40 |
| 2020/0027560 A1 | 1/2020 | Ling et al. | |

(Continued)

OTHER PUBLICATIONS

Yip, Michael, and Nikhil Das. "Robot Autonomy for Surgery." arXiv preprint arXiv:1707.03080 (2017). (Year: 2017).*

(Continued)

*Primary Examiner* — Christopher B Tokarczyk

(57) ABSTRACT

System, methods, and other embodiments described herein relate to autonomous assessment and treatment of a patient. In one embodiment, a method includes, responsive to acquiring, in a managing device, sensor data characterizing a condition of the patient, determining a diagnosis for the condition according to a correlation of the sensor data with a subset of markers. The method includes selecting, using a treatment model, a treatment algorithm from a set of treatment algorithms for performing therapeutic delivery using a robotic device. The method includes causing the robotic device to perform the therapeutic delivery according to the treatment algorithm selected by the treatment model.

20 Claims, 9 Drawing Sheets

(56) References Cited

U.S. PATENT DOCUMENTS

| | | |
|---|---|---|
| 2020/0035335 A1 | 1/2020 | Kivatinos et al. |
| 2020/0098461 A1 | 3/2020 | Macoviak et al. |
| 2020/0111578 A1* | 4/2020 | Koblick ................ G16H 80/00 |
| 2022/0037039 A1* | 2/2022 | Wein ..................... G16H 50/20 |
| 2023/0030273 A1* | 2/2023 | Ortega Quijano ... G06V 10/245 |

OTHER PUBLICATIONS

Sahashi, et al., "A study of operational liability of the medical rescue robot under disaster," 2011 IEEE/SICE International Symposium on System Integration (SII), 2011, 6 pages.

* cited by examiner

PROVIDING HEALTHCARE VIA AUTONOMOUS, SELF-LEARNING, AND SELF-EVOLUTIONARY PROCESSES

TECHNICAL FIELD

The subject matter described herein relates, in general, to improving the implementation of healthcare through the use of autonomous learning systems for monitoring, diagnosing, and providing treatment and, more particularly, to the use of deep reinforcement learning and adaptive models that, implemented through various robotic devices, autonomously provide healthcare to patients.

BACKGROUND

Healthcare represents a myriad of complexities for providing quality care. For example, expenses associated with healthcare continue to rise on a yearly basis. Contributors to costs include direct costs of personnel for doctors, nurses, and other caregivers. These costs continue to grow as the availability of caregivers lessens with increased demand. Moreover, further factors that raise costs include insurance premiums, advanced medicine, new medical devices/procedures that require years of investment to develop, and so on. In addition to costs, the accuracy of care is also a difficulty that influences overall quality. As caregivers may be in limited supply, some caregivers may be overextended by working excess hours, thereby potentially increasing the occurrence of errors. Accordingly, providing quality healthcare can encounter various difficulties.

SUMMARY

In various embodiments, example systems and methods relate to a manner of improving healthcare by implementing autonomous learning systems for monitoring, diagnosing, and providing treatment to patients. As noted previously, the cost of healthcare in the U.S. is increasing at an unsustainable rate. To support, enhance, and mitigate the healthcare burdens, autonomous robots will play an important role in the healthcare system. Using robots to supplement or wholly handle healthcare improves the quality of life and enhances overall healthcare value by leveraging the consistency and predictability of an intelligent robotic system. For example, implementing care and decision making via autonomous robots ensures high quality, convenience & access, fast & accurate code set & service, trust & confidence, and time. Thus, the autonomous robots improve healthcare quality by directly performing patient therapeutics, reducing medical errors, promoting adherence to treatment protocols, and so on. In this way, implementing the intelligent autonomous robots and associated management systems improves the quality of healthcare overall.

In one embodiment, a management system for autonomous assessment and treatment of a patient is disclosed. The management system includes one or more processors and a memory communicably coupled to the one or more processors. The memory stores instructions that, when executed by the one or more processors, cause the one or more processors to, responsive to acquiring sensor data characterizing a condition of the patient, determine a diagnosis for the condition according to a correlation of the sensor data with a subset of markers. The instructions include instructions to select, using a treatment model, a treatment algorithm from a set of treatment algorithms for performing therapeutic delivery using a robotic device. The instructions include instructions to cause the robotic device to perform the therapeutic delivery according to the treatment algorithm selected by the treatment model.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements, or multiple elements may be designed as one element. In some embodiments, an element shown as an internal component of another element may be implemented as an external component and vice versa. Furthermore, elements may not be drawn to scale.

DETAILED DESCRIPTION

Figure 1A:
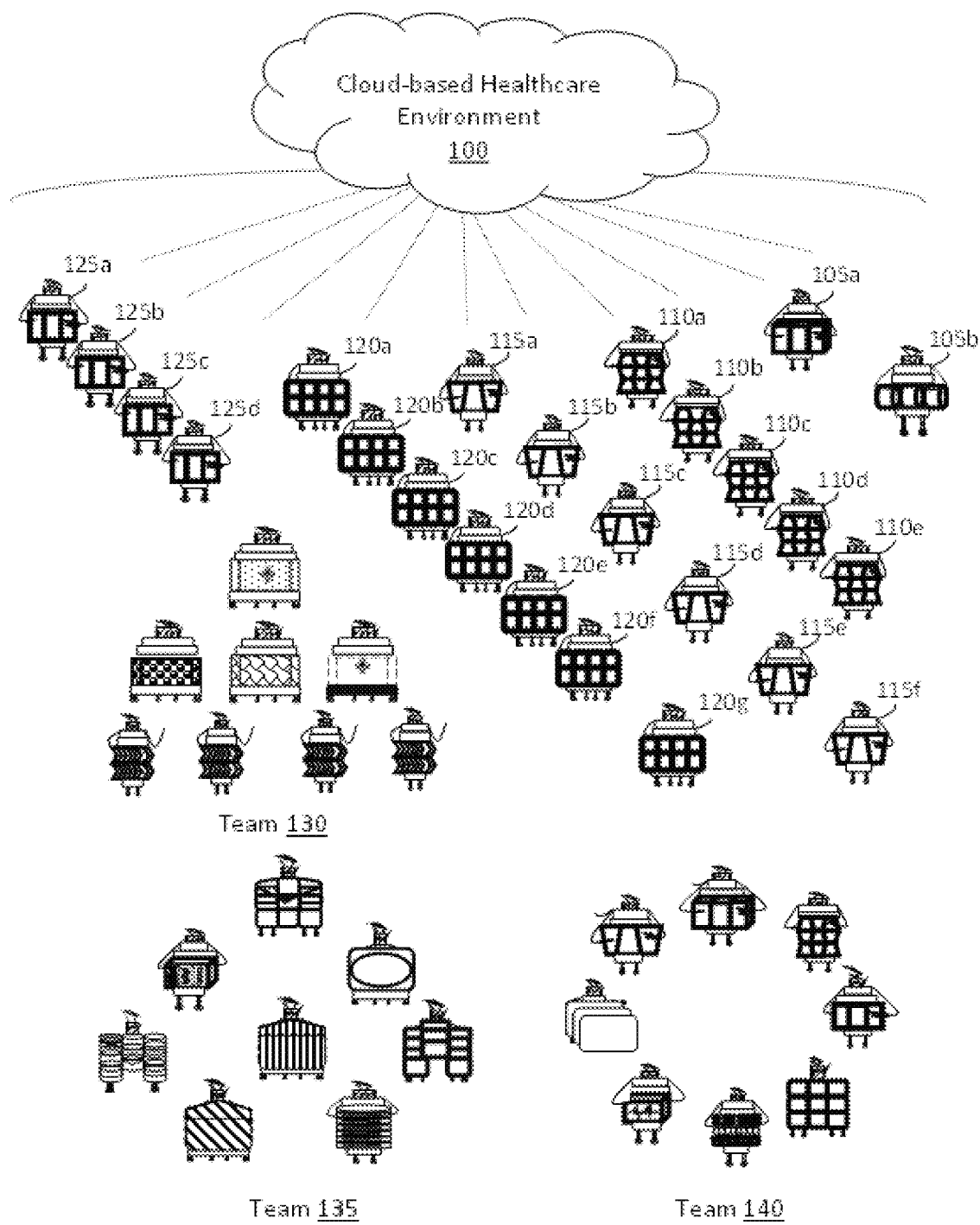
FIG. 1A is a diagram illustrating a cloud-based healthcare environment in which various arrangements of robotic devices interact with patients to deliver care.

Systems, methods, and other embodiments are disclosed for improving healthcare by implementing autonomous learning systems for monitoring, diagnosing, and providing treatment to patients. As previously noted, various aspects of modern healthcare contribute to difficulties in providing quality care across the population. For example, pressures on personnel can negatively impact the accuracy of care, such as fatigue from extended hours and added stressors. Moreover, healthcare costs can create barriers to healthcare for various communities leading to reduced quality of care overall.

Therefore, in at least one embodiment, a management system is disclosed for implementing intelligent autonomous robots that function to alleviate the noted difficulties through directly providing care and automatically evolving understanding of treatments and specific cases to continuously improve accuracy and quality of care. For example, in various aspects, a management system is implemented to control a broad network of autonomous robots. The robots themselves may be varied in form and function but generally operate at the direction of the management system. For example, the management system serves as a central hub to coordinate different robots and centralize decision-making in regard to patient care. As one example, the management system may function to control robots for rescuing, monitoring, and providing treatment. In one implementation, the management system interacts with multifunctional medical robots, specialized medical robots, medical rescue robots, medical lab robots, medical imaging robots, pharmacy robots, surgery robots, preventive medicine robots, intensive care robots, rehabilitation robots, medical innovation robots, and so on.

In general, the autonomous robots communicate with the management system to provide information about a patient and to receive instructions from the management system about how to proceed with treating or otherwise interacting with a patient. Accordingly, in one aspect, the management system acquires sensor data from at least one robot about a condition of a patient. The sensor data can include vitals of the patient, images of the patient, information about why the patient is seeking medical attention, and so on. The management system can then act to diagnose the condition of the patient and also determine how to triage the patient by activating additional autonomous robots. For example, in one approach, the management system uses separate learning models that evolve according to feedback. The models can include separate models for determining algorithms for monitoring, determining a diagnosis, determining algorithms for treatment, and so on. It should be appreciated that while the management system includes the models and trains the models, the implementation of the selected algorithms is carried out by the autonomous robots. That is, the management system uses the models to determine which robots and which algorithms to activate to treat the patient and then evolves the treatment as well as the models themselves according to feedback about the treatment. As such, the management system provides centralized intelligence that is adaptive in relation to the treatment of a given patient and also in the overall understanding of the selection of the algorithms to continuously improve outcomes.

Referring to FIG. 1A, an example cloud-based healthcare environment 100 in which a management system (not illustrated) operates is shown. As shown in FIG. 1, the cloud-based healthcare environment 100 includes connections (e.g., wireless communication links) to a multiplicity of different autonomous robots. In general, the robots are configured to move, manipulate and perform various tasks autonomously, which may be at the initial direction of the management system. As one example, various ones of the robots (e.g., 115a-115f) are configured with multiple degrees of freedom to enable, through the movement of the robots, therapeutic delivery along potential paths within an environment proximate to a patient. The robots position themselves to provide the therapeutic delivery in desired locations (e.g., in a particular position relative to a patient). As shown in FIG. 1A, the cloud-based healthcare environment 100 may include and control many different types of robots. FIG. 1A shows robots 105a-b, 110a-e, 115a-f, 120a-g, 125a-d, and different groups or teams of robots, which may be comprised of the noted robots 105-125 or may include further types of robots. The groups can include specialized care robot team 130, surgery robot team 135, rescue robot team 140, and so on. The teams are generally comprised of an arrangement of different robots that function symbiotically to provide care focused in a particular manner. As one aspect, the management system controls individual robots to group into the teams according to various circumstances, such as the presence of a patient with a particular diagnosis.

Returning to the individual robots, robots 105 may each be configured with claws, opposable grapplers, or other instruments for effecting therapeutic delivery. Broadly, the robots are configured with a combination of software and hardware that providing intelligence within the robots, including perception, understanding, planning, and so on, to actuate a particular included manipulator and other dynamic aspects of the robots in providing care to a patient. To achieve interaction with a patient and provide care, various different ones of the robots include medical sensor sets. A medical sensor set is, in one approach, mounted at a fixed state relative to a base of a robot or other stationary reference point of a robot. Medical sensor sets are, for example, groupings of sensors that include sensors that provide sensor data, including images and/or other data related to shape, color, depth, and/or other features of patient(s) that are in the line of sight of the sensors. Thus, the sensors of a given set may include cameras (e.g., RGB cameras, infrared cameras, etc.), ultrasonic sensors, MMW radar, LiDAR, etc. In further aspects, the medical sensor sets include, for example, monographic cameras, stereographic cameras, and/or 4D laser scanners. A 4D laser scanner includes one or more lasers that emit light and one or more sensors that collect data related to reflections of the emitted light. A 4D laser scanner may be, for example, a time-of-flight 4D laser scanner or a triangulation-based 4D laser scanner and may include a position-sensitive detector (PSD) or another optical sensor as just a few examples.

Dynamic clinical screening, as implemented via the various robots in combination with the management system, relies on sensor data collected by the robots to assist the robots in making informed clinical decisions and enabling automated patient care. From the collected sensor data, the management system and/or another robot codes the perceived information to align with a format of defined markers so that the management system can select one or more algorithms for treating a clinical diagnosis. The algorithms are executed by the various robots at the direction of the management system as a sequence of specified medical treatments or clinical procedures.

At the beginning of a clinical manifestation, real-time clinical evidence collected by the robot is processed, for example, by the management system along with a success signal indicating a readiness of the robot according to a position of the robot relative to the patient. The management system can then select and provide a particular algorithm for drug delivery over a communication network based, at least in part, on the clinical evidence. The selected algorithm via the management system directs the robot to perform drug delivery in a next healthcare delivery cycle of the robot. The clinical treatment is then implemented by the robot. The screening of the robot after implementing the clinical treatment can then be applied as clinical evidence along with the success signal, and an additional drug delivery generated signal over the network. This may continue to be performed iteratively (e.g., at each healthcare delivery cycle of the robot) until the success signal is achieved (e.g., as determined based on a reward satisfying a criteria) and/or other criteria are met. The other criteria can be, for example, that a temporal duration of the clinical manifestations has satisfied a threshold (e.g., X seconds) or that a threshold quantity of healthcare delivery cycles has occurred. At each separate iteration, the management system is acquiring sensor data, including feedback about previous actions and changes in a condition of the patient by which the models may then select different algorithms and/or different therapies to evolve the care of the patient according to perceived changes. Prior to the performance of separate iterations of therapeutic delivery and monitoring by the robots, the robots and/or the management system may update one or more models according to perceived outcomes from a prior timestep or set of timesteps.

Continuing with the collection of the sensor data and diagnosis of the condition of the patient, marker sets and labeling involve, in one approach, a continuous, or at least semi-continuous, flow of clinical data (i.e., sensor data) and evolving treatments between the patient and the robots. In one aspect, the management system functions to iteratively reconfigure robots providing treatment and performing monitoring of the patient according to the sensor data that provides feedback about therapeutic delivery (i.e., treatment). In general, the reconfiguration of the robots by the management system includes selection of algorithms according to the sensor data and, in some cases, activation of additional and/or different robots. That is, as one example, where an active robot is administering a pharmaceutical to the patient and the patient is, for example, not responding to the pharmaceutical, the management system may adapt the algorithm that is active to a different algorithm that provides a different pharmaceutical, a higher delivery rate of the pharmaceutical, and/or a higher dose of the pharmaceutical. In general, the different algorithms are specific to different treatments and embody specific protocols about the delivery of a given therapeutic/treatment.

As a further example, a robot can apply stimulation bio-signals to neural tissue of a patient during drug delivery, and then, based on one or more stimulation bio-signals and observed effects, the robot can observe a level of intensity during drug delivery. The cycle is a feedback loop helping the management system build an understanding of how these therapeutics works. The more perceptions of cycles, the more intelligent the management system and the robot becomes, resulting in a higher accuracy of making clinical decisions and treatments.

The management system improves the performance of the robots using a reinforcement learning process, as described herein, which facilitates rapid learning of clinical outcomes, for performing particular healthcare tasks via the one or more robots. The robots are able to use learned policies to improve accuracy and overall efficiency in providing the healthcare tasks. Healthcare tasks may, for example, be performed by the robots more quickly with an accurate selection of treatments as the reinforcement learning process takes place. Such healthcare tasks may additionally, or alternatively, be performed safer and more effectively or may continue to be carried out within defined therapeutic parameters as other aspects of the robots' performance improves with the learning process.

In various arrangements, as applied herein, autonomous learning and evolution involves clinical data analysis and treatments involving selecting, using, and modifying/correcting algorithms for monitoring and treatment via various analytical models. The noted models can learn from clinical data (i.e., the sensor data via a reinforcement reward function) with minimal manual intervention. As such, the efficiency gains referred to above, in terms of the therapeutic treatments performed by the robots, may frequently occur (i.e., over the treatment of a single patient) as the learning process continues. Overall, the rate at which the performance of the robots improves, along with the resulting efficiency gains, results in the robots carrying out healthcare tasks in an optimal manner in less time than with other learning techniques. It will be appreciated that this results in the above-mentioned advantages, such as improved therapeutic methods at the robots, being experienced at an earlier stage. Thus, parallelizing training across multiple robots, which pool their clinical outcomes, can result in models that select and monitoring therapeutic deliveries that are more accurate and/or robust.

As one example of how the management system defines a goal for improving outcomes with the robots, the management system defines a healthcare function that is optimized as part of the learning process. At screening $x_t$ in time t, the management system chooses and causes a robot to execute a selected treatment $u_t$ according to its clinical outcomes. $\pi(u_t|x_t)$, transitions to a new screening $x_t$ according to dynamics of the robot $p(x_t|x_t, u_t)$, and receives a reward $r(x_t, u_t)$. In general, the goal of reinforcement learning is finding the optimal clinical outcomes. $\pi$, which maximizes an expected sum of rewards from an initial screening distribution. The management system determines the reward, in at least one arrangement, based on the healthcare function, which, as mentioned above, is dependent on the robotic task (i.e., treatment, monitoring, etc.) to be accomplished. Accordingly, reinforcement learning in the robotics context seeks to learn an optimal clinical outcome for the performance of a given robotic task.

To train a model that parameterizes a clinical outcome for determining a robotic clinical treatment based on real-time clinical evidence, the management model leverages available information, including sensor data and observed feedback. Real-time clinical evidence can include the current state of patient(s) in the robot's environment. The model can be a neural network that accepts the real-time clinical evidence (i.e., sensor data or derivations thereof) and that generates, based on the clinical evidence, a clinical treatment/therapeutic delivery, including, for example, drug delivery, surgery, etc. For instance, the drug delivery can indicate velocity commands to be provided to each of the actuators of the robot or torques to be applied to each of the drug delivery of the robot. A robot can utilize a clinical outcome neural network by applying real-time clinical evidence to the clinical outcome neural network at each healthcare delivery cycle of the robot, generating drug delivery by processing the real-time clinical evidence using the clinical outcome neural network, and implementing control commands to effectuate the clinical treatment indicated by the drug delivery. The screening that follows the implementation of the control commands can then be utilized as the real-time clinical evidence in the next healthcare delivery cycle.

Thus, the overall learning process uses the evidence, which is in the form of the sensor data collected by the robots and provided to, for example, the management system via a communication network. To collect datasets for training and learning of the various models, the robots generate instances of datasets during the iterative performance of tasks. The collected datasets are used in the models by iteratively updating the parameters of the models. Training of the models may be asynchronous relative to the generation and collection of the datasets from the multiple robots. That is, threads that train/update the models are decoupled from the threads that generate and/or collect the datasets from the multiple robots. For example, the training/updating threads can operate on one or more processors and the experience threads can operate on one or more additional processors that are separate from the one or more processors operating the training/updating threads. The decoupling between the training and the experience threads can ensure that a difference in training speed and experience collection speed does not halt the control programs of the robots generating the datasets, which are often required to send controls at fixed frequencies. In other words, the decoupling can enable the collection of datasets to continue to occur through corresponding experience threads without halting of those threads for training purposes.

Moreover, the decoupling enables the training threads to operate in parallel with the experience threads, asynchronously and iteratively updating parameters for training the models. Also, in many implementations, the training thread(s) can operate a protocol layer that is greater than one or more of the control frequencies of the robots. In those implementations, real-world training times can be reduced relative to techniques that do not utilize the datasets from multiple robots by obtaining the datasets from multiple robots operating in parallel and by performing the training asynchronously in separate threads. For example, the training can occur without any delays that are due to not having new datasets available in a buffer. Also, for example, the separate threads can prevent the need to halt dataset collection to enable training to occur or vice versa.

Utilization of the datasets from multiple robots and the decoupling of the training and experience collection threads can result in a model that is more accurate and/or robust after a given number of training iterations, which may include datasets from a combination of different robots. Multiple robots generating datasets can operate asynchronously relative to one another and/or the updated clinical outcomes parameters can be provided by the robots asynchronously prior to clinical manifestations performance.

Figure 1B:
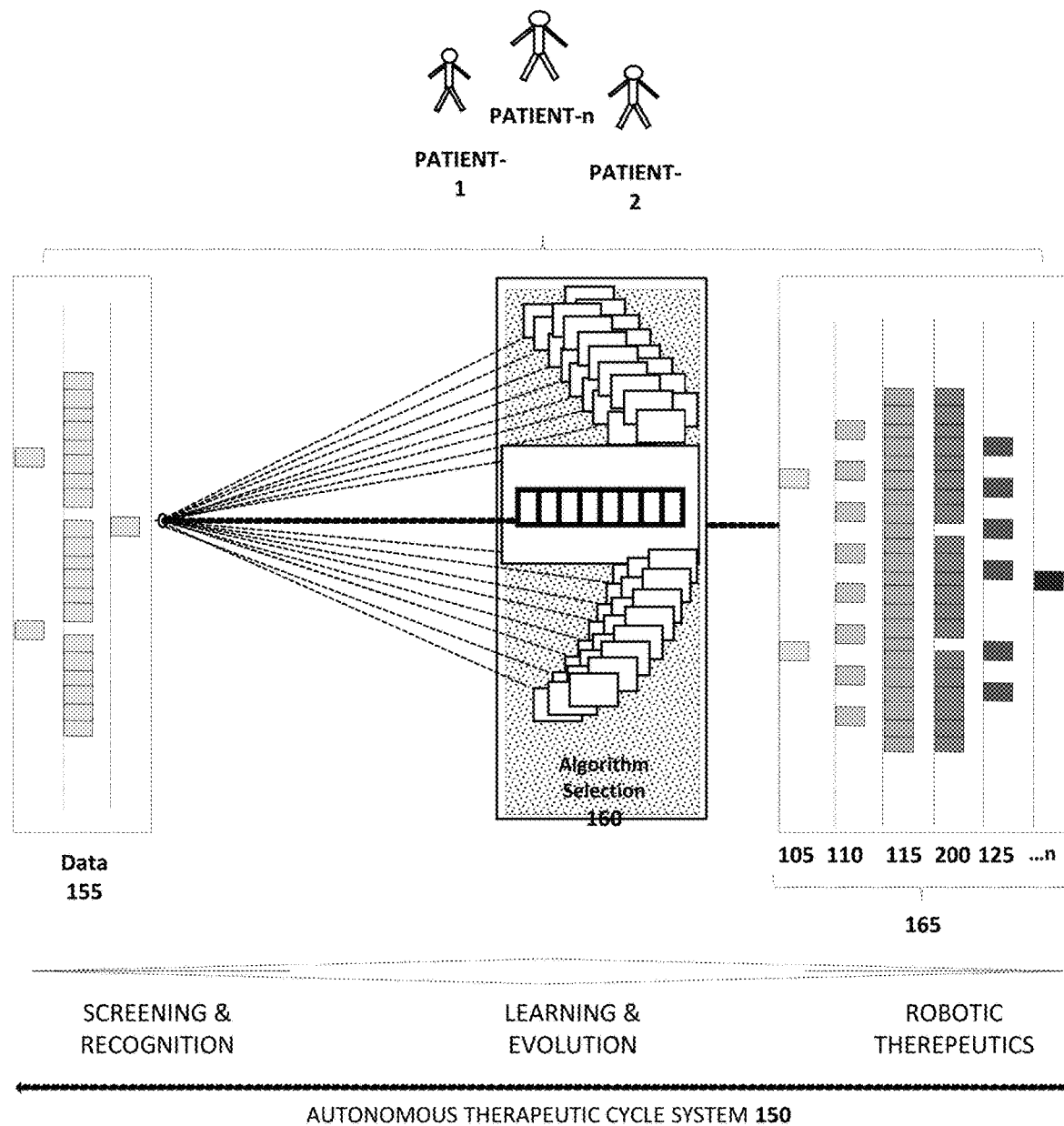
FIG. 1B is a diagram illustrating relationships between different processes of an autonomous therapeutic cycle implemented between a cloud-based management system and various robotic devices.

Turning to FIG. 1B, one example of an autonomous therapeutic cycle 150, which may be implemented along with the cloud-based healthcare environment 100 is illustrated. As illustrated in FIG. 1B, the autonomous therapeutic cycle 150 involves three primary components. The primary components include data 155, algorithm selection 160, and robotic implementation 165. For example, the data 155 corresponds with the collection of sensor data using one or more of the robots 105-125. In general, collection of the data 155 may take different forms and may extend beyond the simple acquisition of the data 155 itself. For example, the robots and/or the management system that is cloud-based may process the raw sensor data into further perceptions/determinations using various processing algorithms (e.g., machine learning algorithms) to derive higher-level information from the raw sensor data. The additional determinations can include identification, classification, correlation, and/or other functions in order to derive characteristics of a condition of a patient from the sensor data. The additional determinations may further be embedded as labels, tags, or other indicators with the sensor data itself. As one example, the additional determinations can include neural network processing of images, such as x-ray or magnetic resonance images (MRIs) in order to identify broken bones, torn tissue, tumors, and/or other abnormalities.

In any case, the initial acquisition of the sensor data embodies screening of the patient and recognition of the condition, which occurs iteratively between the robots and the management system. The information is leveraged by the management system to perform the algorithm selection 160. Thus, the sensor data and derived information may align with a set of markers that correlate with a specific diagnosis. The management system, in one approach, then applies one or more models, such as a deep neural network trained according to reinforcement learning, to the acquired information. The models generate selections of different algorithms for therapeutic delivery (i.e., treatments) to be carried out by the robotic implementation 165.

Additionally, the algorithms themselves and the selection of the algorithms via the models are subject to a process of learning and evolution that improves the overall ecosystem of the autonomous therapeutic cycle 150. That is, the management system uses the data 155 provided as feedback to algorithm selections to adapt the algorithms themselves according to a performance of the algorithm and also to adapt the selection of the algorithms according to an accuracy of the selection. As will be discussed in greater detail subsequently, the management system and/or the robots 165 can institute reward functions as part of reinforcement learning (e.g., double Q reinforcement learning) to iteratively train and improve the noted models/algorithms.

Figure 2:
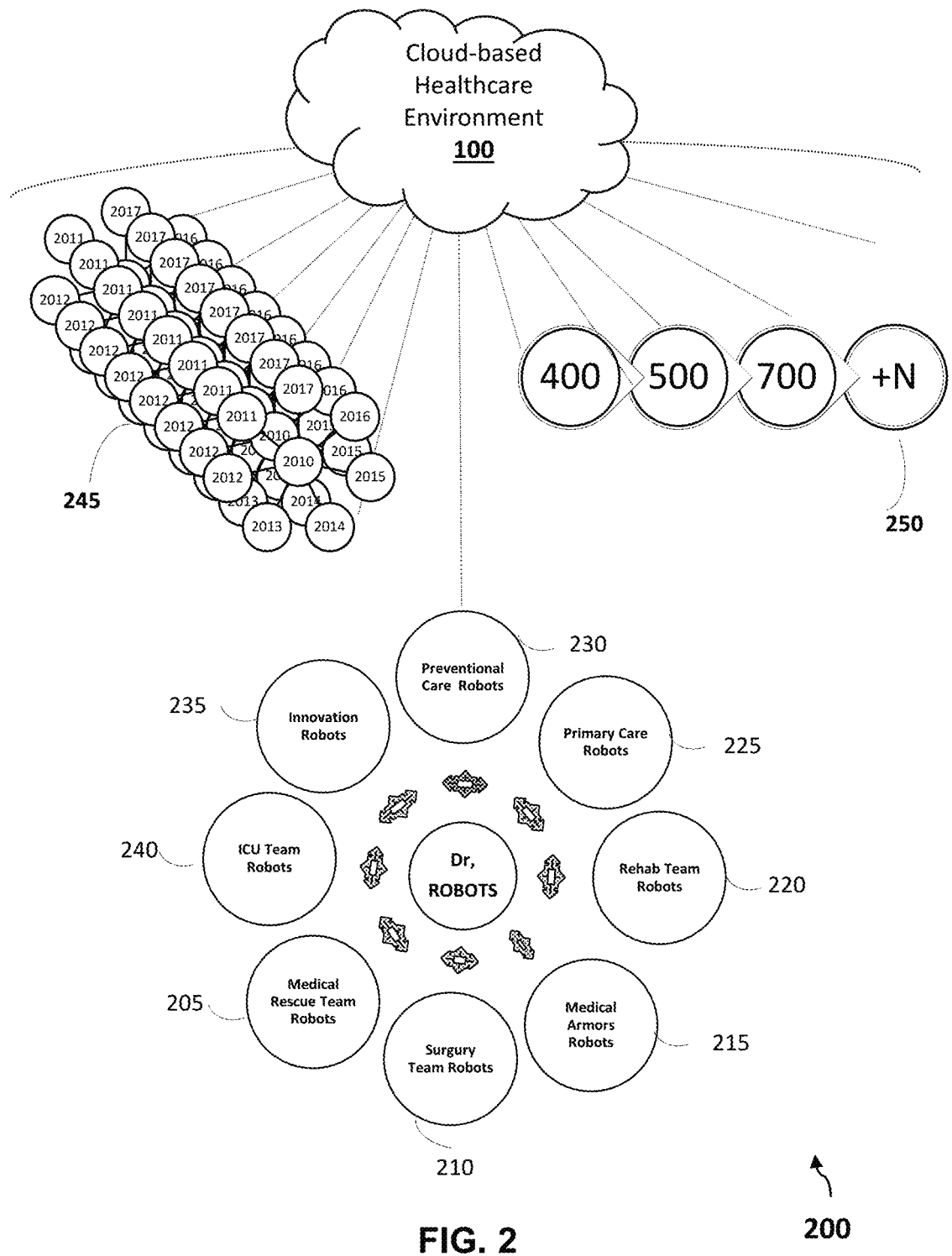
FIG. 2 illustrates a diagram of associations between different elements in a cloud-based healthcare environment.

FIG. 2 illustrates an example of how the management system in combination with the various robotic devices perform an autonomous self-selecting, self-assembling, self-disassembling, self-learning, and self-evolution process 200. As shown, selection and control of individual ones of autonomous healthcare robots 205, 210, 215, 220, 225, 230, 235, and 240, which generally align with robots 105-125 as shown in FIG. 1A, is based on concepts of biological evolution. A clinical outcome of possible therapeutic treatments and clinical procedures to the clinical evidence is first screened with separate treatments being scored using a biological function that indicates quality of a respective outcome. Collected datasets about separate treatments can indicate a corresponding initial screening, a subsequent screening embodying results of initial treatments, clinical treatments relating to the initial screening, and rewards for the clinical treatment. The clinical treatment executed to transition from the initial screening to the subsequent screening can be generated based on processing of the initial screening using, for example, a treatment model, which is a neural network in one example. Thereafter, the treatment model can be updated according to observed outcomes from subsequent screening and derivation of outcome parameters for the corresponding clinical manifestations. The reward for the clinical treatment can be generated based on a healthcare function for the reinforcement learning.

FIG. 2 further represents medical algorithm set selection 245. The management system implements one or more models to perform (e.g., treatment model, monitoring model, etc.) to choose an algorithm for treatment/monitoring according to, for example, a current status/condition of the patient. While one algorithm may perform well in some patients, the same algorithm may perform poorly in others. Thus, the management system functions to identify when to use which algorithm according to acquired information about the patient, thereby optimizing implemented algorithms for separate scenarios and improving overall clinical outcomes.

As further illustrated, FIG. 2 represents robot and robot team selection 250. Accordingly, in various arrangements, the management system implements one or more functions (e.g., a machine learning model, a heuristic-based function, etc.) to choose a medical robot or robot team from a multifunction robot or swarm of robots when selecting monitoring and treatment algorithms for a patient. The selected robots/teams function to implement Autonomous Therapeutic Procedures (ATP) defined by the algorithms for treating a diagnosed condition of the patient. ATPs encompass a variety of procedures, ranging from the administration of prescription drugs (drug delivery) to surgical procedures to psychotherapy.

Figure 3:
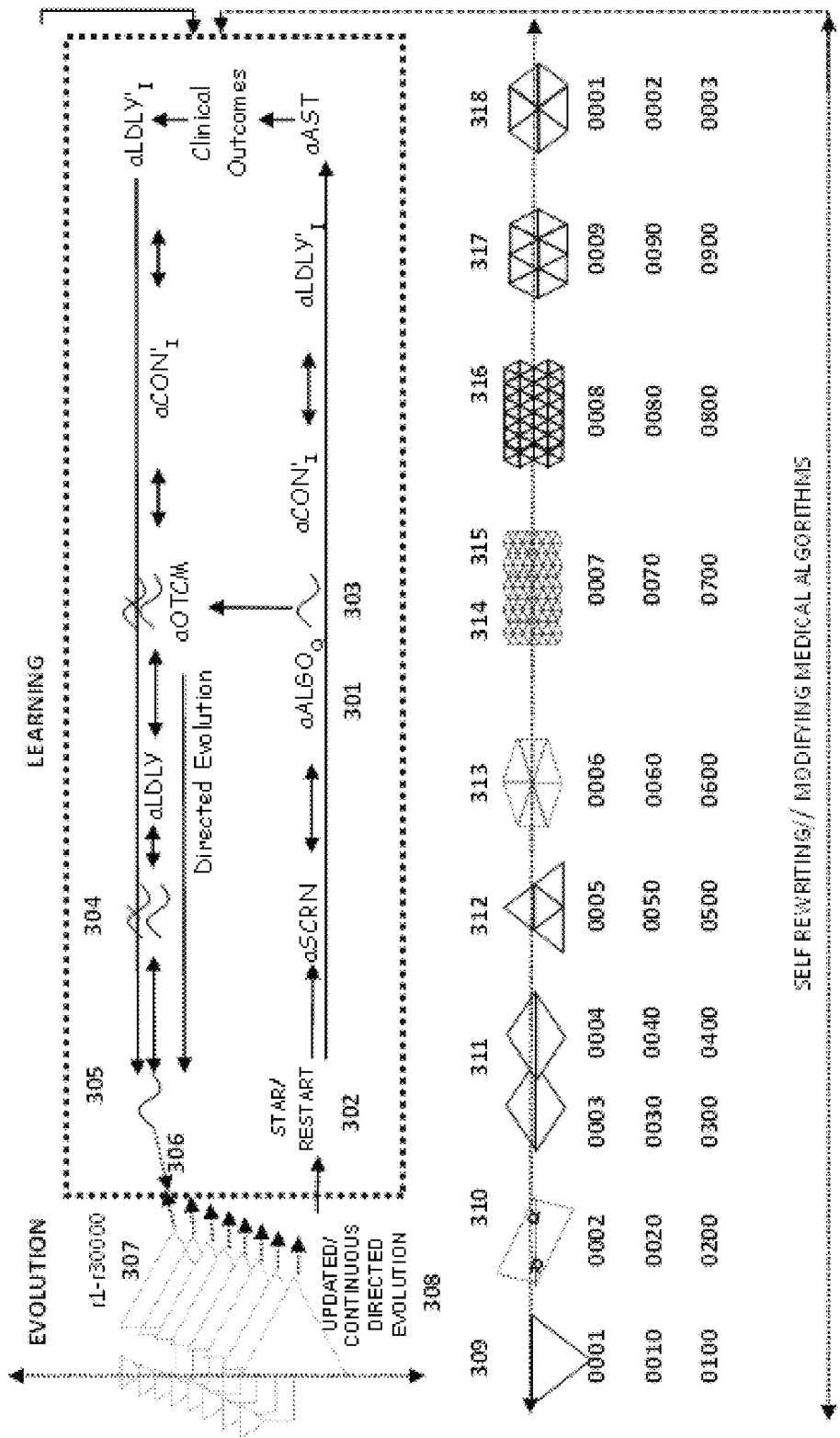
FIG. 3 illustrates a diagram about learning and evolution associated with the training of various algorithms and models.

FIG. 3 illustrates general processes for self-learning and self-evolution of systems in the cloud-based healthcare environment 100. In particular, FIG. 3 shows a diagram 300 for training a particular algorithm 301. As an aside on the form of the algorithm 301 itself, the algorithm 301 may include a medical algorithm encoding model, a medical code encoding model, a state encoding model, and a decoder. Additionally, the medical algorithm encoding model is, in one approach, constructed based on a pre-trained deep Q learning. The medical code encoding model, the state encoding model, and the decoder are, for example, language models based on a recurrent neural network, and the medical code encoding model may further comprise a question encoder and a fact encoder. Accordingly, the algorithm 301 is trained based on deep reinforcement learning and evolution programming, where an optimization process is undertaken until a value of a hybrid loss function does not decrease or fall below a preset value.

In FIG. 3, a series of steps 302-307 are shown within a learning block that embodies this process. At, step 302, the management system initiates learning through the instantiation of the algorithm 301 and particular inputs, such as a medical code for training the algorithm 301. The medical code may be derived from a particular dataset describing a condition of a patient and associated environment. At 303, the algorithm 301 executes over the medical code to generate an output. Additionally, at 303, the system uses the medical algorithm encoding model to encode medical algorithms to generate a first vector and to obtain a first vector set. Thereafter, at step 304, the system fuses the first vector set using the question encoder, the fact encoder, and the state encoding model to encode rounds of dialogues of the dialogue medical codes in the first dialogue medical code set into state vectors corresponding to a round sequence and obtaining a first state vector set.

At 305, the system uses the first state vector set to generate answers corresponding to the round sequence by the decoder, obtains a second answer medical code set, and uses the first state vector set to generate a second medical algorithm vector set by a single-layer perception mapping function. At 306, the management system calculates a probability that all medical algorithm vectors in the second medical algorithm vector set belong to a physical environment vector by the clinical outcome, uses the probability and the first answer medical code set to optimize the therapeutic model, and obtains a first optimized therapeutic model. At 307, the management system samples the first medical algorithm vector set and the second medical algorithm vector set, generates an adversarial training sample pool to optimize the discriminator, and obtaining a first optimized clinical outcome at 308. Updated parameters can then be applied to algorithm 301 to realize the learning.

As further shown in FIG. 3, elements 309, 310, 311, 312, 313, 314, 315, 316, 317, and 318 further include determining a violation of one or more criteria for a given robot, in a given iteration of a treatment, modifying the treatment of the given iteration so that the one or more criteria are no longer violated, and generating a given instance of the datasets based on the modified treatment. The criteria can include one or more of: joint position limits, joint velocity limits, and end effector positional limits. Overall, FIG. 3 illustrates a diagram representing separate processes for learning, evolution, and swarm intelligence associated with the training of various algorithms and models.

Figure 4:
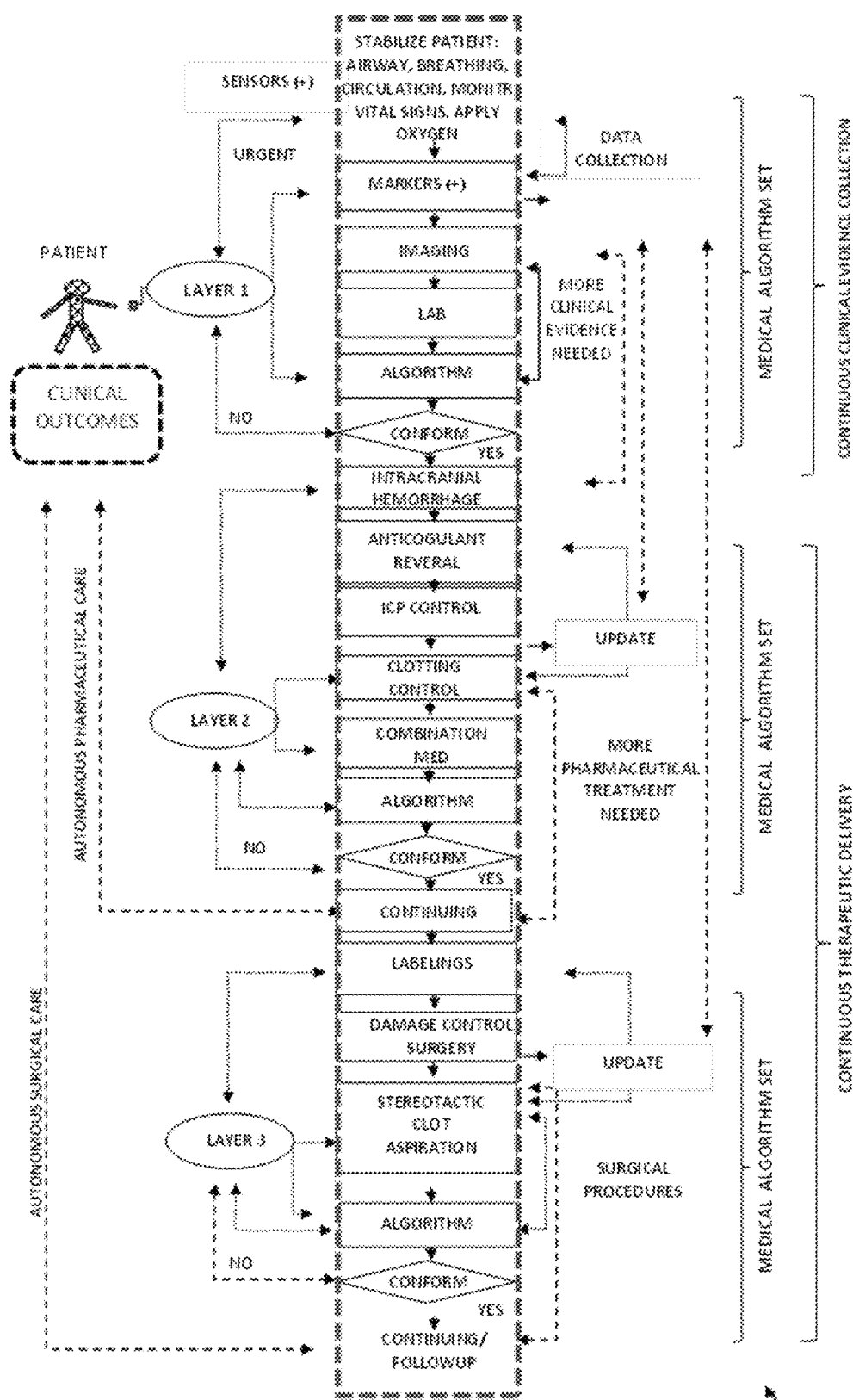
FIG. 4 depicts an example architecture of autonomous healthcare command and control for a patient with multiple traumatic injuries.

FIG. 4 schematically depicts an example architecture 400 of autonomous healthcare command and control as may be implemented by a management system. FIG. 4 further focuses on one example scenario for a patient with multiple traumatic injuries. Accordingly, the management system implements self-trained diagnostic and treatment algorithms according to, for example, a reinforcement learning approach as discussed with FIG. 4.

In some implementations, the management system functions to receive a given instance of a clinical dataset from one or more robots that are, for example, monitoring or otherwise stated as collecting clinical evidence by a given robot of a plurality of robots. A robot generates the given instance of the clinical dataset when performing a task as, for example, directed by the management system (e.g., screening and triaging a patient). The management system can further receive additional instances of clinical datasets from additional robots that may supplement the other robot or perform separate functions, such as testing, treatment, and so on.

Overall, as shown in FIG. 4, the management system operates to manage robots that are providing care to the patient. A primary aspect of providing the care is to collect diagnostic information, as shown in layer 1. Layer 1 generally functions to continuously collect evidence via one or more robots about a condition of a patient in the form of sensor data that may be derived into various observations. As discussed herein, the use of the term "continuous" generally means according to an on-going iterative process that repeats the collection of the sensor data to monitor changes in the condition and a response of the patient to the administration of treatments by the various robots. Accordingly, as shown, one or more robots perform the data collection and may further locally process the collected data to derive additional determinations from the information. As noted previously, the derivations may vary but generally include detection, identification, classification, and so on. That is, the particular robot that is acquiring the sensor data may implement different processing routines, such s machine learning algorithms, to extrapolate information from the sensor data.

In any case, the robots may collect data according to various sensors or other devices. As shown in FIG. 4, the robots may perform different types of imaging (e.g., different medical imaging techniques), lab processing of blood or other samples from a patient, and so on. The management system acquires the information and may generate a diagnosis or multiple diagnoses according to correlations with known subsets of markers for different conditions. Moreover, the management system can then perform a selection of one or more algorithms for subsequent data collection using a monitoring model. The monitoring model processes a context defined by, for example, the previously collected data, currently connected data, prior/current treatments, and/or other data inputs about a condition of the patient and treatments. As an output, the monitoring model provides a selection of one or more algorithms, which are communicated to the appropriate robots to then implement in monitoring and/or retrieving additional information about the patient. Layers 2 and 3 are similar processes for different types of therapeutic delivery. That is, the management system acquires diagnoses information and identifies different treatments that are to be performed by various robots. The treatments correlate to different algorithms that are selected. The management system can then select the treatments and identify whether results conform with expectations. According to the results, the reinforcement learning generates updated parameters that are used to train the models selecting the algorithms for treatment and monitoring/screening in addition to updating the algorithms themselves according to performance. In this way, the management system in combination with the distributed robots are able to improve clinical outcomes.

The medical algorithms implemented by the robots and selected by the management system are trained by deep reinforcement learning to improve the operational performance of one or more robots. As previously described, the implementations provide operational advantages, such as efficiency gains in the therapeutic treatments carried out by the robots, and also mitigate drawbacks of prior robotic applications of reinforcement learning. These may include mitigating the need for clinical outcome representations and/or mitigating the need for human-supplied demonstrations. In some implementations, a clinical outcome neural network that parameterizes the clinical outcome is trained through deep reinforcement learning, which mitigates the need for hand-engineered clinical outcome representations. Moreover, the clinical outcome neural network can be model-free in that it does not explicitly learn a model of a robotic environment.

As one particular example, in some implementations, deep reinforcement learning algorithms based on non-clinical outcome training using Medical Algorithm Evolutionary Deep Reinforcement Learning (MAEDRL) can scale to complex 4D manipulation tasks and can learn deep neural network policies efficiently to train based on clinical datasets. In some implementations, parallelizing the algorithm across multiple systems (e.g., robots) can additionally and/or alternatively result in the clinical outcome neural network being more accurate and/or robust after a given number of training iterations. This can be due, for example, clinical datasets from multiple sources being used to train the network.

In various implementations, reinforcement learning is extended to learn complex manipulation policies, which are beyond the learning of treatment protocols, monitoring, and algorithm selection. In some implementations, the complex manipulation policies are learned without healthcare demonstrations and/or are learned using neural network representations that do not require task-specific domain knowledge. Also, in some of those various implementations, the policies are learned using a non-clinical outcomes MAE-DRL algorithm, such as a deep deterministic clinical outcomes Gradient algorithm or a Normalized Advantage Function algorithm. For example, asynchronous deep reinforcement learning may be utilized, such as asynchronous deep reinforcement learning that uses a parallel Normalized Clinical Function (NCF) algorithm across a plurality of robots. In one aspect, training in this way enables sample-efficient training on real robotic platforms, greater time-efficiency in training by using the shared experience of multiple robots, and/or more robust training due to variations between the multiple robots and/or different environments. The improved time-efficiency of the training results in, for example, the robots using the improved policies to carry out healthcare tasks at an earlier time.

In some implementations, pooling experience from multiple simulated robots reduces overall training time under the assumption that simulation time is inexpensive and the training is dominated by neural network backpropagation. In contrast, some implementations minimize the training time when training based on data from real physical robots, where experience is expensive and neural network backpropagation is comparatively cheap. For example, various implementations collect clinical datasets from multiple robots that operate asynchronously from one another. Moreover, various implementations use the clinical datasets in training a clinical outcome neural network asynchronously from the operation of the multiple robots. For example, a buffer of the clinical datasets can be utilized to update the clinical outcome neural network. In this manner, collection of clinical datasets can be asynchronous among multiple robots and asynchronous to the updating of the clinical outcome neural network.

Some implementations disclosed herein may focus on model-free reinforcement learning, which includes clinical outcome search methods and value-iteration methods. While clinical outcome search methods offer a direct way to optimize a true objective, they may require significantly more data than value iteration methods because of on-clinical outcome learning. Accordingly, some implementations disclosed herein focus particularly on value iteration methods, such as value iteration methods based on MAE-DRL with function approximation. Two examples of value iteration methods are Deep Deterministic Policy Gradient (DDPG) and NCF, which extend deep MAEDRL to a continuous clinical treatment space and are more sample-efficient than competing clinical outcome search methods due to, for example, non-clinical outcome learning through a replay buffer. DDPG is an algorithm that concurrently learns a Q-function and a policy using patient history and the Bellman equation to learn the Q-function, which can then determine treatments.

The goal in reinforcement learning is to control a robot attempting to maximize a healthcare function which, in the context of a robotic function, denotes a healthcare definition of what the robot should try to accomplish. At screening $x_t$ in time t, the robot chooses and executes clinical treatment $u_t$ according to its clinical outcome $p_t$. ($u_t|x_t$), transitions to a new screening $x_t$ according to the dynamics p ($x_t|x_t, u_t$), and receives a reward r ($x_t, u_t$). In some implementations described herein, infinite-horizon discounted return problems are considered.

In at least one embodiment, for learning, the techniques described herein utilize a Medical Algorithm Evolutionary Deep Reinforcement Learning (MAEDRL) that provides data efficiency gains as compared to clinical outcome variants. Extensions of MAEDRL with function approximation may be utilized in various implementations to avoid issues with intractability. Two examples of extensions of MAE-DRL with function approximation are DDPG and NCF. DDPG circumvents the intractability problem by adopting a therapeutic robot-critic method, while NCF restricts classes of MAEDRL to enable closed-form to update as in the discrete clinical treatment case. During exploration, a temporally correlated noise may optionally be added to the clinical outcome network robot drug delivery.

For many real-world healthcare tasks, the techniques described herein can be applied to autonomous systems to learn a variety of robotic skills defined by healthcare functions, such as the delivery of various treatments. However, the learning process is typically time-consuming. Accordingly, in various arrangements, a parallelized variant of NCF or a parallelized version of DDPG to improve learning. This may enable learning a neural network parametrized MAE-DRL from scratch on complex real robot healthcare tasks aligning with different treatments or portions thereof. In practical deep robotic learning applications, the learning time is, in one example, constrained by the data collection rate of real robots, which may be limited to real-time rather than network training speed. Accordingly, various implementations disclosed herein propose the use of asynchronous NCF to effectively use multiple real robots for data collection and increase the real-world speed of learning. This, of course, achieves a more rapid improvement in real-world robot performance, together with corresponding efficiency gains, as previously discussed, when the learned policies are implemented by the robots carrying out healthcare tasks. Moreover, various implementations disclosed herein achieve aggressive exploration during MAEDRL, which may be beneficial and/or required when learning from scratch. In some of those implementations, techniques may also be employed to achieve aggressive exploration while minimizing or preventing violation of one or more criteria of the robots performing the exploration.

In implementations of asynchronous NCF disclosed herein, trainer thread(s) (that update/train the clinical outcome neural network) are, for example, separated from the experience collector thread(s) (which each collect healthcare delivery cycle clinical datasets from one or more robots during exploration). In some of those implementations, the decoupling between the training and the collector threads may ensure that the difference in training speed does not halt control programs of the robots generating the clinical datasets. While the trainer threads keep training from a replay buffer (populated by experience collector threads, the experience collector thread(s) sync their clinical outcome parameters with the trainer thread(s) at the beginning of separate iterations, execute commands on the robots, and push instances of clinical datasets into the replay buffer.

Presented below is an overview of one example algorithm for performing asynchronous NCF with N collector threads and one training thread. Although the example algorithm is presented with one training thread, in some implementations, multiple training threads may be provided.

In various implementations, a neural network may parametrize the clinical treatment-value functions and policies. In some implementations, various screening representations may be utilized as clinical evidence to the model in generating a drug delivery that is indicative of a clinical treatment to be implemented based on the policies. The screening representations can indicate the screening of the robot and optionally the screening of one or more environmental, clinical conditions. As one example, a robot screening representation may include joint angles and end-effector positions, as well as their time derivatives. In some implementations, a success signal may be appended to a robot screening representation.

In one approach, the success signal may be utilized in determining a reward associated with training a particular model for a clinical treatment and/or for other purposes. The particular success signal will depend on the task for which reinforcement learning is taking place. For example, for a reaching task that is part of a treatment, the success signal may be the goal/target position for the end-effector. As another example, for a drug delivery task, the success signal may include the handle position when the dosage is adjusted, and the quaternion measurement of a sensor. In various implementations, feed-forward networks can be utilized as a clinical outcome neural network to parametrize the clinical treatment-value functions and policies. As one example, two-hidden-layer network with a size of 100 units each may be used to parametrize each of m(x), L(x) (Cholesky decomposition of P(x)), and V(x) in NCF and m(x) and Q (x; u) in DDPG. For Q (x; u) in DDPG, the clinical treatment vector u may be added as additional clinical evidence to a second hidden layer followed by a linear projection. ReLU may be used as hidden activations and hyperbolic tangent (Tan h) may be used for final layer activation in robots m(x) to bound the clinical treatment scale.

As a further example of parameters of an algorithm for controlling a robot that may be dynamically adapted according to the reinforcement learning, in at least one approach, parameters include torque values for actuators, end-effector velocity, end-effector position relative to a target position, attributes of robot joints during motion (e.g., position, velocity, and acceleration of joints/end-effector), and so on. The above is a non-exhaustive list. It should be appreciated that further parameters can include timing, the motion of the robot itself, position of sensors, control of treatment-specific devices (e.g., hypodermic needles), etc.

Moreover, to update an algorithm may use the gradient of the loss function with respect to the parameters. For instance, the system may update the target clinical outcome network based on: '. rarw..tau..theta..sup. Q+(1−.tau.)'. For example, hemorrhagic shock is one of the central problems in patients with multiple trauma and a common cause of death. Increasing clinical and research interest in the specific role of posttraumatic coagulopathy state that the first step is to identify the source of bleeding. If the patient does not respond to nonsurgical measures (volume replacement, compensation of acidosis, etc.) as treated according to an initial selection of treatment algorithms, then surgical hemostasis is recommended through a subsequent selection of different algorithms. During the shock room phase, the patient's coagulation parameters (prothrombin time, partial thromboplastin time, thrombocyte count, fibrinogen, and/or viscoelastic procedures) should be determined and any necessary corrective treatment initiated. However, improvement of coagulation must not be delayed by laboratory analyses. These various considerations are embodied in aspects of the selected algorithms according to the treatment.

Additionally, the target systolic blood pressure in seriously injured patients with hemorrhagic shock is 80 to 90 mm Hg. In the presence of severe head injury, the systolic blood pressure should be kept >80 mm Hg. Restrictive volume replacement with the above-mentioned target values should be carried out using crystalloid solutions. Packed red cells and fresh frozen plasma should be transfused in a fixed ratio of 2:1 to attain a hemoglobin concentration of 70 to 90 g/L. Alternatively, fibrinogen and PRC can be given. The initial dose of fibrinogen should be 3 to 4 g in the presence of pathological viscoelasticity or a plasma fibrinogen level <1.5 to 2.0 g/L. The thrombocyte count should generally be 50×109/L; with persistent hemorrhage or in the presence of head injury, the target is 100×109/L. All of the noted aspects for the treatment are accounted for in the algorithms implemented via the management system to cause the various robots to monitor the particular physiological aspects of the patient's condition and provide the treatment in a specific way.

As a further example, the algorithms further account for the administration of tranexamic acid regarding antifibrinolytic medication in the shock room is recommended for all patients with manifest or threatened hemorrhagic shock. The initial infusion of 1 g tranexamic acid over 10 minutes should be followed by administration of a further 1 g over the next 8 hours. In patients with persistent bleeding and thrombocyte function disorders (disease-related or drug-induced), thrombocyte function should be determined, and thrombocytes transfused if required. Administration of desmopressin in a dose of 0.3 µg/kg is reserved for patients with von Willebrand-Jürgens syndrome and those being treated with thrombocyte aggregation inhibitors. Factor VIIa should be given to patients with heavy bleeding and persistent coagulopathy only after exhaustion of all alternative measures. Thus, the algorithms account for the noted treatment plans in relation to all different conditions of a patient, including specific aspects to monitor, particular ways in which a therapeutic is to be delivered, including timing and other considerations, and also aspects relating to particular control of the robot itself, including positioning, movements, etc.

To provide some additional detail on implementations described herein, some example healthcare tasks that may be learned through reinforcement learning techniques disclosed herein are described in more detail. Some examples of healthcare tasks include random target reaching, drug delivery, including increasing the dosage and/or decreasing the dosage, and pick and place. For example, in a reaching task, a robot arm may try to reach a random target in space from a fixed initial configuration. A random target is generated per clinical manifestations by sampling points uniformly from a cube of size 0.2 m centered around a point. The random target may be provided as the success signal. Given the end-effector position e and the target position y, the healthcare function may be r (x; u)=c.sub.1d (y; e(x)) c.sub.2u.sup.Tu.

Also, for example, in a dosage and drug delivery task, a robot may try to release a drug by increasing the dosage or decreasing the dosage of the drug delivery via the robot. The handle can be turned downward for up to 90 degrees, while the drug delivery can be released up to 90 degrees in both directions. The drug delivery has a spring such that it closes gradually when no force is applied. The drug delivery has a latch such that it could release the drug delivery when the handle is turned past approximately 60 degrees. A medical sensor set attached to the drug delivery can be used for drug delivery angle measurements, and quaternion readings from the medical sensor set can be used to compute the loss. For example, the healthcare function can be composed of two parts: the closeness of the end-effector to the handle, and the measure of how much the drug delivery is released in the right direction. The first part of the healthcare function depends on the patient's state during medical screening. The second part of the healthcare function depends on the composition such as drug, polymer, and additives, their ratio, physical and/or chemical interactions among the components q, and its value when the drug delivery is released q.sub. Accordingly, while the description describes various tasks that may be implemented by the robots via algorithms selected by the management system, the noted tasks are not an exhaustive listing but are merely exemplary.

Autonomous Healthcare (AH) is a robotic healthcare system, which includes automated and/or autonomous systems to deliver healthcare via defined therapeutics.

Autonomous Healthcare and Payment Platform (AHPP) is a robotic platform that can include an Algorithm-Based, Outcome Targeted, Systems Oriented, Evidence Driven (AOSE) autonomous therapeutic system for treating disease with little or no human input.

Autonomous Therapeutics Delivery Cycle (ATDC) within the system, takes place repetitively. The more the number of Perception-Action Cycles take place, the more intelligent an agent becomes, resulting in a higher accuracy of making decisions, especially in complex therapeutics situations.

Autonomous Medical Screening (AMSS) is a method using robotics, data processing/control software, liquid handling devices, and sensitive detectors, for detecting disease or body dysfunction. Screening tests are usually administered to individuals without current symptoms, but who may be at high risk for certain adverse health outcomes.

Autonomous Clinical Evidence Recognition (ACER) is a process using machine learning and cognitive technology to identify and categorize unstructured data into specific classifications. The unstructured data includes medical images, pathological sound, bio-signals or quantitative data, and so on.

Autonomous Disease Identification (ADID) is a process that involves identifying and extracting data and performing a clinical diagnostic selection for separate stages of patient care, including predisposition, prevention, diagnostics, treatment monitoring and prognosis.

Autonomous Medical Screening and Recognition (AMSR) refers to a system-based process generating a group of predictions about patients that specifies a number of phenomena in the past, present, and future, with or without interventions of various kinds. AMSR serves as a data collection and updates function to correlate changes used to update algorithms.

Autonomous Healthcare Learning and Evolution System (AHLE) is an algorithm-based platform including Medical Algorithm Evolutionary Deep Reinforcement Learning (MAEDRL). MAEDRL occurs repetitively. The more occurrences of the therapeutics delivery cycle that take place, the more intelligent robots become, resulting in a higher accuracy of making decisions, especially in complex therapeutics situations. The greater the number of connected therapeutics, the greater the number of therapeutics experiences are recorded, enabling the healthcare robots to make decisions based on data generated by multiple autonomous therapeutics.

Autonomous Therapeutics are robotic treatments used to alleviate or prevent a particular disease. Examples of therapeutics include drug therapy, medical surgeries & procedures, nutrition therapy, stem-cell therapies, and combination therapies.

Figure 5:
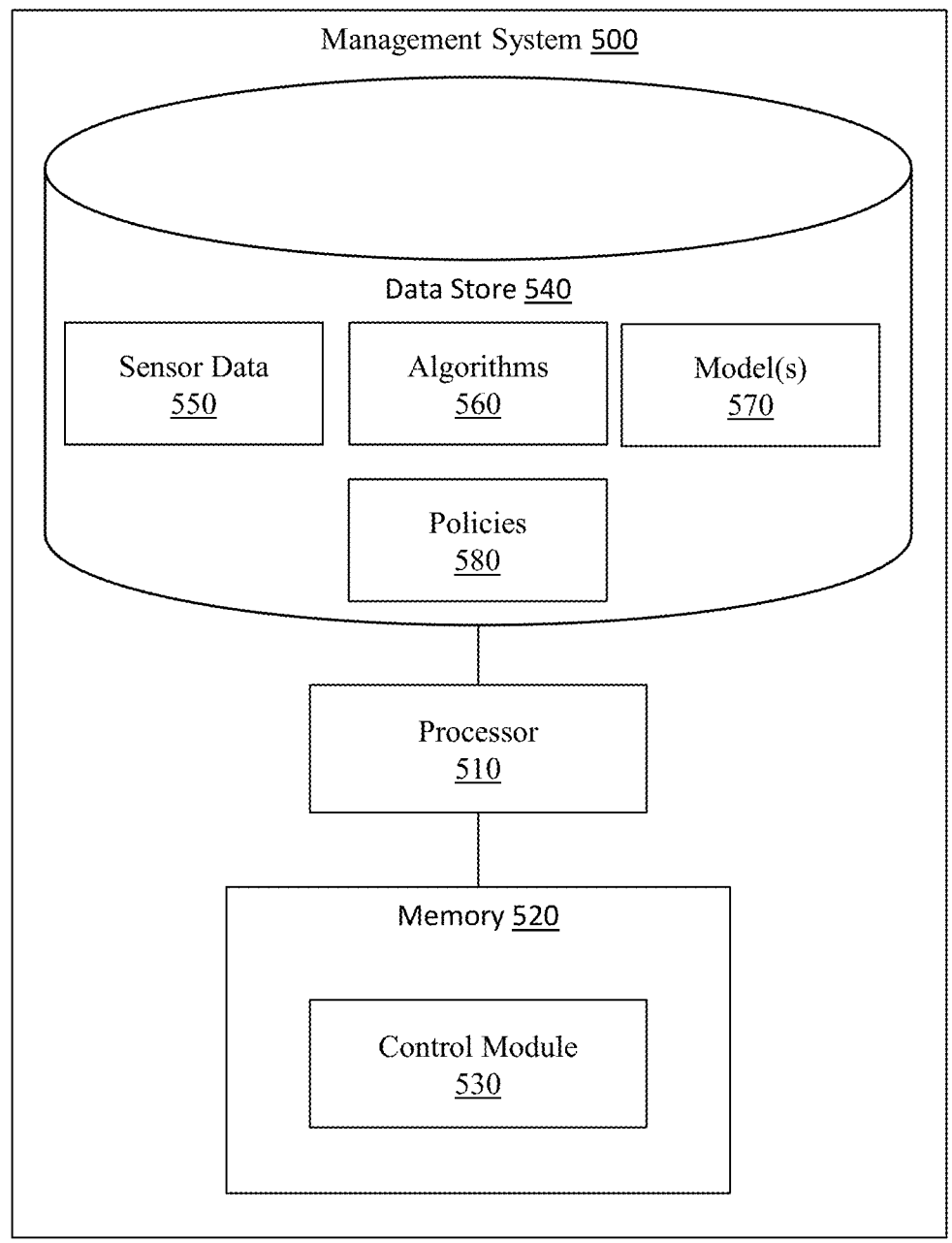
FIG. 5 illustrates one embodiment of a management system associated with autonomous assessment and treatment of a patient.

With reference to FIG. 5, one embodiment of the management system 500 is further illustrated. The management system 500 is shown as including a processor 510 1. Accordingly, the processor 510 may be a part of the management system 500 or the management system 500 may access the processor 510 through a data bus or another communication path as a shared resource (e.g., a distributed processing environment). In further aspects, the processor 510 is a cloud-based resource. Thus, the processor 510 may communicate with the management system 500 through a communication network or may be co-located with the management system 500. In one embodiment, the management system 500 includes a memory 520 that stores a control module 530. The memory 520 is a random-access memory (RAM), read-only memory (ROM), a hard-disk drive, a flash memory, or other suitable memory (either volatile or non-volatile) for storing the control module 530 and/or other information used by the management system 500. The control module 530 is, for example, computer-readable instructions within the physical memory 520 that, when executed by the processor 510, cause the processor 510 to perform the various functions disclosed herein.

Continuing with FIG. 5 and a general embodiment of the management system 500, in one or more arrangements, the management system 500 includes a data store 540. The data store 540 is, in one embodiment, an electronic data structure (e.g., a database) stored in the memory 520 or another electronic memory and that is configured with routines that can be executed by the processor 510 for analyzing stored data, providing stored data, organizing stored data, and so on. Thus, in one embodiment, the data store 540 stores data used by the module 630 in executing various functions. In one embodiment, the data store 540 includes the sensor data 550, algorithms 560, models 570, and policies 580 along with other information that is used by the module 630. It should be appreciated that while the data store 540 is shown as including the sensor data 550, separate instances of the management system 500 may implement the data store 540 to include additional sets of information, such as metadata and/or derived information associated with the sensor data 550, additional models/functions, and so on.

In any case, the control module 530 includes instructions that function to control the processor 510 to acquire the sensor data 550 from various robots that implement monitoring and treatment of patients. To acquire the sensor data 550, the management system may include or at least functions in cooperation with a communication system. In one embodiment, the communication system communicates according to one or more communication standards. For example, the communication system may be wired, wireless, or a combination thereof. The communication system can include multiple different antennas/transceivers and/or other hardware elements for communicating at different frequencies and according to respective protocols, whether wired or wireless. The communication system, in one arrangement, communicates via a communication protocol, such as a WiFi, DSRC, V2I, V2V, or another suitable protocol for communicating between the management system 500 and the respective robots. Moreover, the communication system, in one arrangement, further communicates according to a protocol, such as the global system for mobile communication (GSM), Enhanced Data Rates for GSM Evolution (EDGE), Long-Term Evolution (LTE), 5G, or another communication technology that provides for the management system 500 communicating with various remote robots. In any case, the management system 500 can leverage various communication technologies to provide communications to other entities and/or received information from other entities.

The management system 500 acquires the sensor data 550 that, in one arrangement, the robots process into determinations about a condition of the patient, including identification of physiological states, perceptions of various sensors, derivations/results of different tests, images, labs, and so on. In general, the sensor data 550 embodies observations of the different robots in treating and monitoring the patient. In general, the management system 500 may acquire any information generated by the robots as being complementary to the sensor data 550 as part of the sensor data 550 itself. Thus, the sensor data 550 is not limited to including only observations from cameras, LiDAR, radar, medical imaging devices, lab test sensors, physiological monitoring sensors, and similar sensors about the patient but can also include information derived therefrom resulting from processing by different models (e.g., machine learning algorithms, statistical analysis functions, etc.).

The control module 530, in one arrangement, while not necessarily directly controlling the robot or the sensors of the robots may induce various robots to activate sensor readings or perform various analyses to derive information through, for example, selection of algorithms for the robots to implement. The control module 530 may further process the sensor data 550 into separate observations about the patient. For example, the control module 530, in one approach, fuses data from separate sensors to provide an observation about a particular aspect of the patient and/or may bridge information between different robots to facilitate combined observations. In any case, the control module 530 includes instructions that cause the processor 510 to acquire the sensor data 550.

In regards to the algorithms 560, the algorithms 560, as previously described in relation to FIGS. 1-6, include algorithms for controlling various robots to perform monitoring of patients and treatment of patients. Thus, the algorithms generally define protocols for controlling the robots, protocols for performing treatments, control structures for how a robot operates to achieve the noted protocols, different characteristics of an associated monitoring/treatment routine, and so on. The management system 500 uses the models 570 to analyze the sensor data 550 and select which of the algorithms 560 to activate among a selection of robots available at the patient. Of course, as outlined above, the algorithms 560 are learning algorithms that are trained via a reinforcement learning approach in at least one configuration. Additionally, the models 570, which may include at least a monitoring model and a treatment model are, in at least one arrangement, also learning algorithms. The models 570 may learn according to reinforcement learning or another approach, such as supervised learning. In any case, the policies 580 define, for example, reward functions for implementing reinforcement learning. Thus, the policies 580 facilitate self-learning and evolution of the management system 500 and associated robots in providing autonomous healthcare to patients. Therefore, the management system 500 and the robots function symbiotically to improve patient care through the disclosed learning framework.

Figure 6:
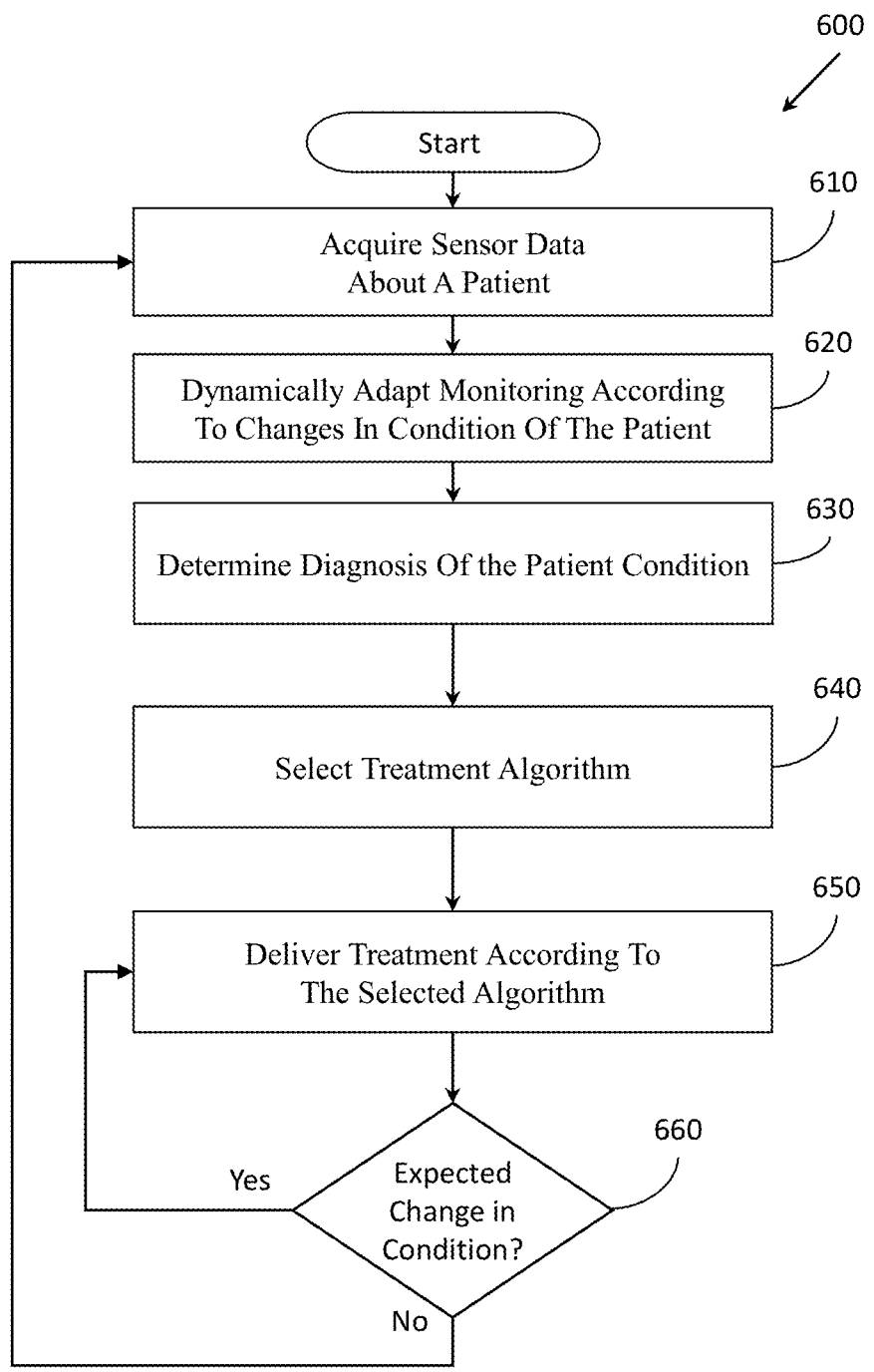
FIG. 6 is a flowchart illustrating one embodiment of a method associated with autonomous assessment and treatment of a patient.

Additional aspects about autonomous healthcare using robotic devices will be described in relation to FIG. 6. FIG. 6 illustrates a flowchart of a method 600 that is associated with autonomous assessment and treatment of a patient using a self-learning approach. Method 600 will be discussed from the perspective of the management system 500 of FIG. 5 as implemented within the cloud-based healthcare environment 100 of FIG. 1. While method 600 is discussed in combination with the management system 500, it should be appreciated that the method 600 is not limited to being implemented within the management system 500 but is instead one example of a system that may implement the method 600. Furthermore, while the method is illustrated as a generally serial process, various aspects of the method 600 can execute in parallel to perform the noted functions.

At 610, the control module 530 acquires the sensor data 550 characterizing a condition of the patient. The condition of the patient, as used herein, generally refers to a health of the patient in relation to current wellness both physically and mentally. Thus, the condition of the patient relates to physical traumas/injuries, illness, and so on. The control module 530 receives the sensor data 550 from robotic devices that are interacting with the patient. In one approach, at first contact, a particular robotic device, which may be a triage device, initially acquires the sensor data 550 about the patient so that initial determinations about the condition can be made. It should be appreciated that the control module 530 may be iteratively updated with subsequent acquisitions of the sensor data 550 so that the patient can be iteratively screened and monitored for changes in the condition. In this way, the robotic devices in combination with the management system remain informed about the condition of the patient in order to adapt monitoring and treatment in real-time as needed.

At 620, the control module 530 dynamically adapts monitoring of the patient. In one aspect, the control module 530 performs one or more of the functions of the method 600 in parallel. Thus, while the processes of acquiring the sensor data 550, adapting monitoring, determining a diagnosis, and so on are generally described and illustrated in a serial manner, the separate processes may function in parallel and, for example, in response to changes in the condition of the patient over subsequent iterations of receiving the sensor data and determining the diagnosis. Thus, it should be appreciated that the sensor data 550 may be acquired in a nearly continuous manner such that, for example, dynamically adapting the monitoring occurs with a similar frequency in order to maintain awareness about the patient.

In general, the control module 530 dynamically adapts monitoring according to the condition of the patient. That is, the control module 530, in one approach, uses a monitoring model to assess the sensor data 550, and, in at least one approach, a diagnosis in order to determine how to monitor the patient. That is, different injuries, illnesses, and so on generally correspond to monitoring different aspects of a patient. That is, while some conditions may involve monitoring, for example, blood oxygen levels, heart rate, blood pressure, etc. other conditions may instead focus on patient body temperature or other specific lab work. Accordingly, each separate condition and individual aspects of the condition may warrant different monitoring. As such, the monitoring model, which is, in one approach, a machine learning model, learns the correlations between conditions and monitoring regimes. Therefore, the monitoring model accepts the specified information as an electronic input and generates an indication of how to monitor the patient.

The control module 530 uses the output of the monitoring model to select a monitoring algorithm that is specific to the condition of the patient and focuses monitoring on aspects that are particular to the patient. The monitoring algorithms, as previously outlined, encompass a wide variety of functions. In general, the monitoring algorithms include algorithms for taking vitals, performing labs, and generally acquiring information about the patient. Thus, the control module 530 via the monitoring model may select a plurality of different algorithms. Additionally, while an individual robotic device may implement one or more of the selected monitoring algorithms, the control module 530 may use multiple different robotic devices to achieve the monitoring. Thus, as part of dynamically adapting the monitoring, the control module 530, in one approach, communicates the selected algorithms to different respective devices in order to induce the appropriate monitoring. In this way, the management system 500 autonomously monitors and assesses a patient without manual intervention.

At 630, the control module 530 determines a diagnosis for the condition according to a correlation of the sensor data 550 with a subset of markers. The markers are, in one arrangement, biomarkers that are measurable indicators of some biological state. Thus, the biomarkers separately correspond with different biological processes, pathogenic processes, pharmacologic response, and so on. By way of example, the markers include specific values of chemicals in samples, such as blood, urine, etc. The markers further include values of different vitals of a patient, such as blood pressure, blood oxygen levels, heart rate, and so on. Thus, the markers are generally defined values of observed characteristics of a patient as embodied by the sensor data 550. Moreover, while the sensor data 550 is described in a discrete manner, it should be appreciated that for purposes of monitoring and treatment, the sensor data 550 generally encompasses past observations as well as current observations that may be extended into changes and/or a history of a particular aspect of the patient. Thus, the markers can include markers that extend beyond instantaneous physiological attributes of the patient to encompass time series data and/or other aggregations of information. In any case, the control module 530 generates a diagnosis that characterizes the condition of the patient by comparing the sensor data 550 against the defined markers. In further arrangements, the process of determining the diagnosis may alternatively be performed by one or more of the robotic devices.

At 640, the control module 530 selects, using a treatment model, a treatment algorithm from a set of treatment algorithms for performing therapeutic delivery using a robotic device. Similar to the process of selecting the monitoring algorithm at 620, the control module 530 also uses the sensor data 550 along with the diagnosis to determine a treatment, which generally includes selecting one or more treatment algorithms for performing the treatment. Accordingly, the control module 530, in one approach, applies a treatment model to the diagnosis and the sensor data 550 to determine which of the treatment algorithms is predicted to resolve the condition when implemented by the robotic device functioning autonomously to care for the patient. The treatment model is one of the models 570, which is a machine learning algorithm that learns which of the treatment algorithms to apply according to a response of the condition to a treatment associated with the treatment algorithm. That is, the treatment model is trained to recognize which treatment is appropriate according to the diagnosis and the sensor data 550 so that the management system 500 can autonomously select the treatment via the treatment algorithm and control associated robotic devices to perform the treatment.

Additionally, as with the monitoring, the control module 530 also adaptively implements the treatment according to feedback observed in the patient. That is, as a treatment is delivered via a set of robotic devices implementing the selected treatment algorithms, the control module 530 may receive updated sensor data 550 that reflects changes in the condition. Accordingly, depending on the changes, the treatment model may determine that altering the treatment is appropriate according to a revised output of a different set of treatment algorithms. Thus, the control module 530 effectively implements a feedback loop to monitor and adapt the treatment of the patient in real-time so as to deliver precise and accurate treatment.

At 650, the control module 530 causes the robotic device to perform the therapeutic delivery according to the treatment algorithm. In general, the control module 530 achieves the implementation of the therapeutic by electronically communicating a control signal to the robotic device that induces the robotic device to operate autonomously to treat the patient according to the treatment algorithm. This may involve communicating the selected algorithm or at least an identifier of the selected algorithm to the robot that induces the robot to activate a treatment process. In further aspects, the control module 530 may also provide a portion of the sensor data 550 that is relevant to providing the treatment, such as, for example, information about an injury, imaging labs, and so on. Thus, the information communicated by the control module 530 is generally related to the specific treatment algorithms that are being executed.

At 660, the control module 530 further determines whether the treatment induces an expected change in the patient. In one approach, the control module 530 receives feedback from the robotic device about the performance of the treatment algorithm. That is, the control module 530 may acquire a positive indication about the delivery of the treatment or may acquire further sensor data 550. If the treatment proceeds as expected, then, in one arrangement, the treatment may continue as defined. Otherwise, the control module 530 adapts the treatment according to revised sensor data 550 and further determinations about adapted monitoring and treatment as discussed previously at 620 and 640. In this way, the management system 170 provides a robust mechanism for treating a patient that adapts in real-time and without manual intervention while further learning from prior cycles and actively training the algorithms and models 570 to improve.

Figure 7:
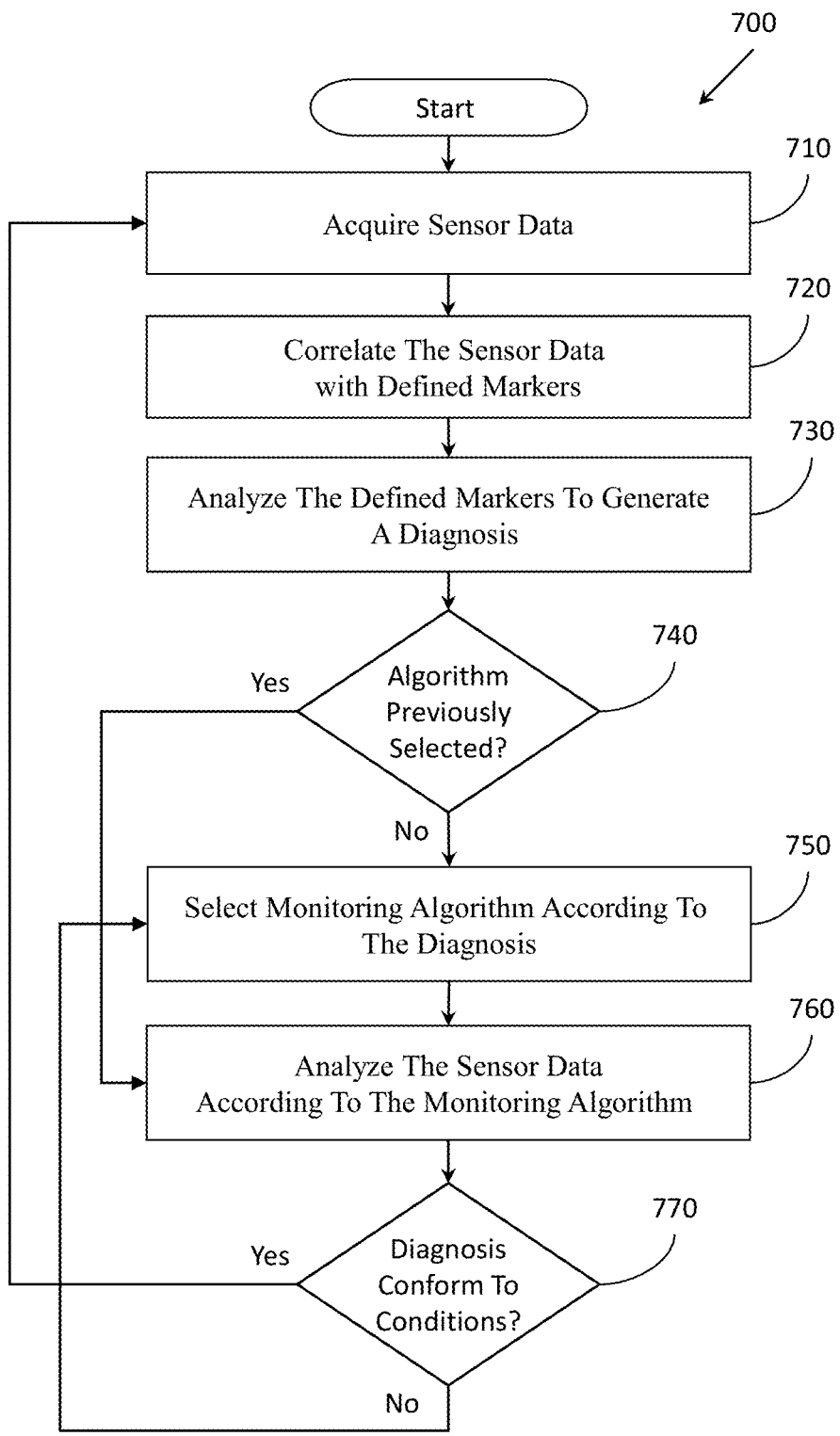
FIG. 7 is a flowchart illustrating one embodiment of a method associated with autonomous monitoring of a patient and learning from feedback about previous monitoring cycles.

Additional aspects of adaptively monitoring a patient will be described in relation to FIG. 7. FIG. 7 illustrates a flowchart of a method 700 that is associated with dynamically adapting monitoring of a patient. Method 700 will be discussed from the perspective of the management system 500 of FIG. 5 as implemented within the cloud-based healthcare environment 100 of FIG. 1. While method 700 is discussed in combination with the management system 500, it should be appreciated that the method 700 is not limited to being implemented within the management system 500 but is instead one example of a system that may implement the method 700. Furthermore, while the method is illustrated as a generally serial process, various aspects of the method 700 can execute in parallel to perform the noted functions.

At 710, similar to block 610 of FIG. 7, the control module 530 acquires the sensor data 550. As noted previously, the acquisition of the sensor data 550 is iterative and occurs such that the block 710 may be executed in parallel with other aspects of the method 700 so that the control module 530 is kept aware of any changes in the condition of the patient.

At 720 and 730, as discussed at 630 of FIG. 7, the control module 530 generates a diagnosis for the patient. As previously noted, the process of generating the diagnosis involves correlating the sensor data 550 with known markers, determining which of the markers match, and analyzing the matching markers to identify a diagnosis (i.e., an illness or injury). As with other aspects of the management system 500, the management system 500 may learn the correlations and improve the identification of various conditions over time through the collection of the diagnosis information in relation to the sensor data 550 and subsequent confirmation through responses of treatments. The management system 500 can define various policies to reward the functions for proper selection and thereby train a model that performs the diagnosis.

At 740, if a monitoring algorithm was previously selected, then the control module 530 can proceed with analyzing the sensor data 550 via the monitoring model at 760 and determine the conformance of the diagnosis to the conditions of the patient. The control module 530 can then adapt the monitoring if the previously selected algorithm does not conform or continue with monitoring. In any case, the process of determining the conformance can be used as a data point in subsequently updating the monitoring model to, for example, determine if the original selection was accurate or not.

At 750, the control module 530 selects the monitoring algorithm from among a plurality of available algorithms. It should be appreciated that the available algorithms, in one or more examples, may further relate to available robots and sensors of the available robots. Because each separate facility may have a different availability of robotic devices and the monitoring is then subject to limitations of the facility, the control module 530 may further consider which robots, sensors, labs, etc., are available and then provide a selection of the algorithms that best fits the condition. In any case, the control module 530 uses the monitoring module to generate a selection and then communicates the selection to the robots.

At 760, in one approach, the control module 530 analyzes the sensor data 550 according to the selection of the monitoring algorithm and any feedback. This analysis may generate a performance score or other policy-based indicator that can then be subsequently used to adapt the monitoring model.

At 770, the control module 530 determines whether the diagnosis and the selection of the algorithm conform to the conditions. If not, then the control module 530 may select a different algorithm. Otherwise, monitoring can continue through provisioning the robot and collecting the sensor data 550. It should be noted that this indication of conformance as discussed at 760-770 can serve as a point to improve the functioning of the management system 500 by learning appropriate selections. In this way, the management system 500 provides for ongoing learning and evolution of the monitoring and assessment process.

Figure 8:
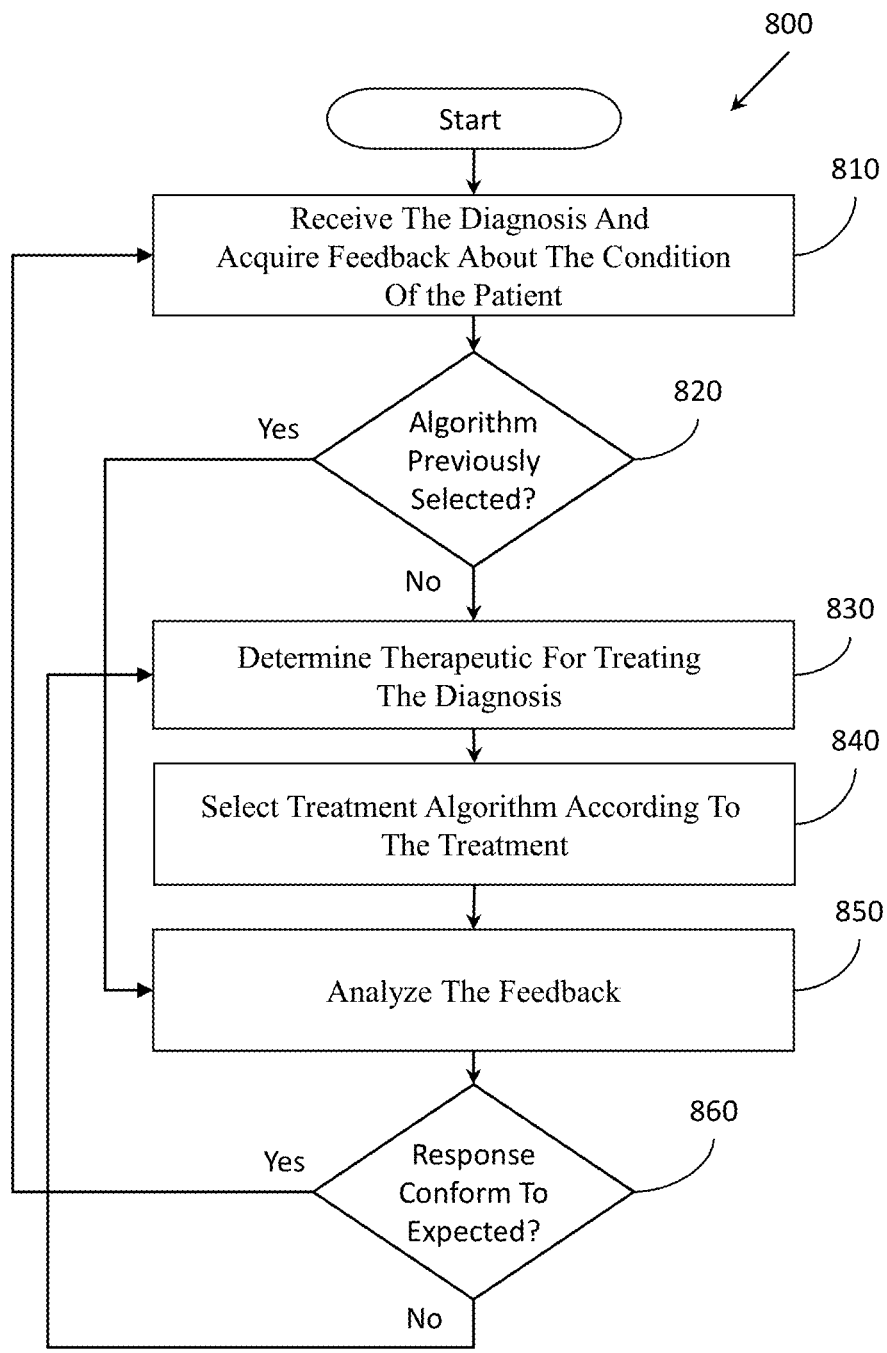
FIG. 8 is a flowchart illustrating one embodiment of a method associated with the autonomous treatment of a patient and learning from feedback about previous treatment cycles.

Additional aspects about selecting treatments will be described in relation to FIG. 8. FIG. 8 illustrates a flowchart of a method 800 that is associated with the autonomous treatment of a patient using robotic devices. Method 800 will be discussed from the perspective of the management system 500 of FIG. 5 as implemented within the cloud-based healthcare environment 100 of FIG. 1. While method 800 is discussed in combination with the management system 500, it should be appreciated that the method 800 is not limited to being implemented within the management system 500 but is instead one example of a system that may implement the method 800. Furthermore, while the method is illustrated as a generally serial process, various aspects of the method 800 can execute in parallel to perform the noted functions.

At 810, the control module 530 acquires information about the diagnosis and the condition of the patient, including, for example, feedback about separate iterations of monitoring. In general, the process of acquiring the sensor data 550 and generating the diagnosis involves blocks 710-730, as discussed with FIG. 8, and serves as an input to method 800.

At 820, if the treatment algorithm was previously selected, then the control module 530 proceeds to block 850 where feedback (e.g., a subsequent iteration of sensor data 550) is analyzed. Otherwise, the control module 530 proceeds with determining a therapeutic as discussed at blocks 830 and 840.

At 830, the control module 530, similar to selecting a treatment algorithm at block 640 of FIG. 7, determines a therapeutic for treating the diagnosis. It should be appreciated that determining a therapeutic/treatment and selecting a treatment algorithm may be a multi-part process depending on the particular implementation. In one approach, the treatment model may determine the therapeutic and the algorithm as a two-part output. That is, there may be multiple options for treating a single diagnosis. Thus, the treatment model, in one approach, accepts the diagnosis and the sensor data 550 as an electronic input at 830 and generates a treatment or multiple possible treatments at 830 that are to remedy the diagnosis of the patient. It should be appreciated that while discussed as singular discrete instances, a single treatment may be a complex assortment of different tasks that are to be administered over time and can include, for example, surgical procedures and pharmaceutical delivery to the patient.

At 840, the control module 530 selects one or more treatment algorithms. As noted, as a second part of the treatment model processing the sensor data 550 to generate the selection, the treatment model, in one approach, may use additional inputs, such as information about a facility and the availability of different equipment and robots to implement the different therapies. Accordingly, using the noted information, the control module 530 applies the treatment model and outputs a selection of the treatment algorithms.

At 850, the control module 530, in one approach, analyzes the sensor data 550 according to the selection of the treatment algorithm and any feedback. This analysis may generate a performance score or other policy-based indicator that can then be subsequently used to adapt the treatment model.

At 860, the control module 530 determines whether the selection of the algorithm conforms to the conditions. If not, then the control module 530 may select a different algorithm at 830-840. Otherwise, monitoring can continue through provisioning the robot and performing the treatment. It should be noted that this indication of conformance, as discussed at 850-860, can serve as a point to improve the functioning of the management system 500 by learning appropriate selections. In this way, the management system 500 provides for ongoing learning and evolution of the monitoring and assessment process. Moreover, the derived information about the conformance is generally based on a reward function for a reinforcement learning policy of the policies 580 and is leveraged for the training of the models 570.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-8, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product that comprises all the features enabling the implementation of the methods described herein and, when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain or store a program for use by or in connection with an instruction execution system, apparatus, or device.

Generally, modules, as used herein, include routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™ Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A management system for autonomous assessment and treatment of a patient, comprising:
    one or more processors; and
    a memory communicably coupled to the one or more processors and storing instructions that, when executed by the one or more processors, cause the one or more processors to:
        responsive to acquiring sensor data characterizing a condition of the patient, determine a diagnosis for the condition according to a correlation of the sensor data with a subset of markers, wherein the instructions to acquire the sensor data further include instructions to select a monitoring algorithm to monitor the patient according to a monitoring model that selects the monitoring algorithm to focus monitoring of the patient on the condition from a plurality of monitoring algorithms for controlling different robotic devices;
        select, using a treatment model, a treatment algorithm from a set of treatment algorithms for performing therapeutic delivery using a robotic device, including applying the treatment model to the diagnosis and the sensor data to identify a two-part output that includes the treatment algorithm and a therapeutic, the treatment algorithm defining how the robotic device is to provide the therapeutic, wherein the instructions to select the treatment algorithm include instructions to select the robotic device from a group of robotic devices and selecting the treatment algorithm according to the robotic device; and
        cause the robotic device to perform the therapeutic delivery according to the treatment algorithm selected by the treatment model by electronically communicating a control signal to the robotic device that induces the robotic device to operate autonomously to treat the patient according to the treatment algorithm, wherein the treatment model and the monitoring model are machine-learning algorithms.

2. The management system of claim 1, wherein the instructions include instructions to select the treatment algorithm including instructions to apply the treatment model to the diagnosis and the sensor data to determine which of the treatment algorithms is predicted to resolve the condition when implemented by the robotic device functioning autonomously to care for the patient, and
    wherein the treatment model is a machine learning algorithm that learns which of the treatment algorithms to apply according to a response of the condition of the patient to a treatment associated with the treatment algorithm.

3. The management system of claim 1, wherein the instructions include instructions to select the treatment algorithm including instructions to select the robotic device from the group of robotic devices according to an availability of equipment of separate robots of the group for providing the therapeutic,
    wherein the instructions include instructions to select the treatment algorithm further including instructions to adapt the treatment algorithm to a different algorithm according to feedback observed in the patient,
    wherein the treatment algorithms include algorithms for causing the robotic device to perform pharmaceutical treatments and surgical procedures, and
    wherein the markers correspond with different physiological attributes of the patient and different subsets of the markers correlate with different conditions of the patient.

4. The management system of claim 1, wherein the instructions include instructions to select the monitoring algorithm including instructions to select a monitoring robotic device from a plurality of monitoring devices according to an availability of sensors of separate robots of the monitoring devices for acquiring the sensor data according to the condition.

5. The management system of claim 4, wherein the instructions include instructions to select the monitoring algorithm include instructions to dynamically adapt monitoring of the patient according to changes in the condition of the patient over subsequent iterations of receiving the sensor data and determining the diagnosis, the sensor data including information about a health of the patient.

6. The management system of claim 1, wherein the instructions include instructions to acquire the sensor data including instructions to receive the sensor data from at least one triage device that is a robotic device operating autonomously to iteratively screen and monitor the patient for changes in the condition,
    wherein the instructions include instructions to acquire the sensor data include instructions to iteratively receive communications from the at least one triage device about the patient, and
    wherein the instructions include instructions to determine the diagnosis including instructions to iteratively analyze the sensor data and adapting the diagnosis to observed changes of the patient.

7. The management system of claim 1, wherein the instructions include instructions to cause the robotic device to perform the therapeutic delivery according to the treatment algorithm including instructions to:
    receive feedback from the robotic device about performance of the treatment algorithm, wherein determining the diagnosis and selecting the treatment algorithm uses the feedback to adapt subsequent iterations.

8. The management system of claim 1, the instructions include instructions to train, using a reinforcement learning policy, the treatment model according to feedback about the patient from the robotic device during treatment according to the treatment algorithm.

9. A non-transitory computer-readable medium storing instructions that, when executed by one or more processors, cause the one or more processors to:

responsive to acquiring sensor data characterizing a condition of a patient, determine a diagnosis for the condition according to a correlation of the sensor data with a subset of markers, wherein the instructions to acquire the sensor data further include instructions to select a monitoring algorithm to monitor the patient according to a monitoring model that selects the monitoring algorithm to focus monitoring of the patient on the condition from a plurality of monitoring algorithms for controlling different robotic devices;

select, using a treatment model, a treatment algorithm from a set of treatment algorithms for performing therapeutic delivery using a robotic device, including applying the treatment model to the diagnosis and the sensor data to identify a two-part output that includes the treatment algorithm and a therapeutic, the treatment algorithm defining how the robotic device is to provide the therapeutic, wherein the instructions to select the treatment algorithm include instructions to select the robotic device from a group of robotic devices and selecting the treatment algorithm according to the robotic device; and cause the robotic device to perform the therapeutic delivery according to the treatment algorithm selected by the treatment model by electronically communicating a control signal to the robotic device that induces the robotic device to operate autonomously to treat the patient according to the treatment algorithm, wherein the treatment model and the monitoring model are machine-learning algorithms.

10. The non-transitory computer-readable medium of claim 9, wherein the instructions include instructions to select the treatment algorithm including instructions to apply the treatment model to the diagnosis and the sensor data to determine which of the treatment algorithms is predicted to resolve the condition when implemented by the robotic device functioning autonomously to care for the patient, and
wherein the treatment model is a machine learning algorithm that learns which of the treatment algorithms to apply according to a response of the condition of the patient to a treatment associated with the treatment algorithm.

11. The non-transitory computer-readable medium of claim 9, wherein the instructions include instructions to select the treatment algorithm including instructions to select the robotic device from the group of robotic devices according to an availability of equipment of separate robots of the group for providing the therapeutic,
wherein the instructions include instructions to select the treatment algorithm further including instructions to adapt the treatment algorithm to a different algorithm according to feedback observed in the patient,
wherein the treatment algorithms include algorithms for causing the robotic device to perform pharmaceutical treatments and surgical procedures, and
wherein the markers correspond with different physiological attributes of the patient and different subsets of the markers correlate with different conditions of the patient.

12. The non-transitory computer-readable medium of claim 9, wherein the instructions include instructions to select the monitoring algorithm including instructions to select a monitoring robotic device from a plurality of monitoring devices according to an availability of sensors of separate robots of the monitoring devices for acquiring the sensor data according to the condition.

13. The non-transitory computer-readable medium of claim 12, wherein the instructions include instructions to select the monitoring algorithm include instructions to dynamically adapt monitoring of the patient according to changes in the condition of the patient over subsequent iterations of receiving the sensor data and determining the diagnosis, the sensor data including information about a health of the patient.

14. A method for autonomous assessment and treatment of a patient, comprising:
responsive to acquiring, in a managing device, sensor data characterizing a condition of the patient, determining a diagnosis for the condition according to a correlation of the sensor data with a subset of markers, wherein acquiring the sensor data and determining the diagnosis further includes selecting a monitoring algorithm to monitor the patient according to a monitoring model that selects the monitoring algorithm to focus monitoring of the patient on the condition from a plurality of monitoring algorithms for controlling different robotic devices;

selecting, using a treatment model, a treatment algorithm from a set of treatment algorithms for performing therapeutic delivery using a robotic device, including applying the treatment model to the diagnosis and the sensor data to identify a two-part output that includes the treatment algorithm and a therapeutic, the treatment algorithm defining how the robotic device is to provide the therapeutic, wherein selecting the treatment algorithm includes selecting the robotic device from a group of robotic devices and selecting the treatment algorithm according to the robotic device; and causing the robotic device to perform the therapeutic delivery according to the treatment algorithm selected by the treatment model by electronically communicating a control signal to the robotic device that induces the robotic device to operate autonomously to treat the patient according to the treatment algorithm, wherein the treatment model and the monitoring model are machine-learning algorithms.

15. The method of claim 14, wherein selecting the treatment algorithm includes applying the treatment model to the diagnosis and the sensor data to determine which of the treatment algorithms is predicted to resolve the condition when implemented by the robotic device functioning autonomously to care for the patient, and
wherein the treatment model is a machine learning algorithm that learns which of the treatment algorithms to apply according to a response of the condition of the patient to a treatment associated with the treatment algorithm.

16. The method of claim 14, wherein selecting the treatment algorithm includes selecting the robotic device from the group of robotic devices according to an availability of equipment of separate robots of the group for providing the therapeutic,
wherein selecting the treatment algorithm further includes adapting the treatment algorithm to a different algorithm according to feedback observed in the patient,
wherein the treatment algorithms include algorithms for causing the robotic device to perform pharmaceutical treatments and surgical procedures, and
wherein the markers correspond with different physiological attributes of the patient and different subsets of the markers correlate with different conditions of the patient.

17. The method of claim 14, wherein selecting the monitoring algorithm includes selecting a monitoring robotic device from a plurality of monitoring devices according to an availability of sensors of separate robots of the monitoring devices for acquiring the sensor data according to the condition,
- wherein selecting the monitoring algorithm includes dynamically adapting monitoring of the patient according to changes in the condition of the patient over subsequent iterations of receiving the sensor data and determining the diagnosis, the sensor data including information about a health of the patient.

18. The method of claim 14, wherein acquiring the sensor data includes receiving the sensor data from at least one triage device that is a robotic device operating autonomously to iteratively screen and monitor the patient for changes in the condition,
- wherein acquiring the sensor data includes iteratively receiving communications from the at least one triage device about the patient, and
- wherein determining the diagnosis includes iteratively analyzing the sensor data and adapting the diagnosis to observed changes of the patient.

19. The method of claim 14, wherein causing the robotic device to perform the therapeutic delivery according to the treatment algorithm includes:
- receiving feedback from the robotic device about performance of the treatment algorithm, wherein determining the diagnosis and selecting the treatment algorithm uses the feedback to adapt subsequent iterations.

20. The method of claim 14, further comprising:
- training, using a reinforcement learning policy, the treatment model according to feedback about the patient from the robotic device during treatment according to the treatment algorithm.

* * * * *